US012708752B2

(12) United States Patent
Rattner

(10) Patent No.: US 12,708,752 B2
(45) Date of Patent: Aug. 18, 2026

(54) PORTACATHETERS WITH IMPROVED STABILITY THAT UTILIZE SMALL INCISIONS AND ARE EASY TO IMPLANT

(71) Applicant: Zachary Rattner, Rancho Santa Fe, CA (US)

(72) Inventor: Zachary Rattner, Rancho Santa Fe, CA (US)

( * ) Notice: Subject to any disclaimer, the term of this patent is extended or adjusted under 35 U.S.C. 154(b) by 0 days.

(21) Appl. No.: 19/052,849

(22) Filed: Feb. 13, 2025

(65) Prior Publication Data

US 2025/0269163 A1 Aug. 28, 2025

Related U.S. Application Data

(60) Provisional application No. 63/659,158, filed on Jun. 12, 2024, provisional application No. 63/644,885, (Continued)

(51) Int. Cl.
*A61M 39/02* (2006.01)
*A61M 5/142* (2006.01)

(52) U.S. Cl.
CPC .................. *A61M 39/0247* (2013.01); *A61M 2005/14284* (2013.01); *A61M 2039/0205* (2013.01);
(Continued)

(58) Field of Classification Search
CPC .......... A61M 39/0247; A61M 39/0208; A61M 2039/0223; A61M 2039/0261; A61M 2039/0282; A61M 2005/14284; A61M 2039/0205; A61M 2039/0211; A61M 2039/0258; A61M 2039/0273; A61M 2039/0276; A61M 2205/04; A61M 39/02
See application file for complete search history.

(56) References Cited

U.S. PATENT DOCUMENTS 5,045,060 A * 9/1991 Melsky ............. A61M 39/0208 604/246
6,319,226 B1 * 11/2001 Sherry .............. A61M 39/0208 604/93.01
(Continued)

FOREIGN PATENT DOCUMENTS

WO WO 2022/245357 A1 * 11/2022 ............ A61M 39/02

*Primary Examiner* — William R Carpenter
*Assistant Examiner* — Robert F Allen
(74) *Attorney, Agent, or Firm* — Haug Partners LLP; Robert E. Colletti

(57) ABSTRACT

Embodiments comprise novel portacatheter structural extensions, wherein a core port with extensions more fully utilizes the port incision, is more stable in the pocket, and fits through the same incision versus the core port without extensions. Extensions resist port flipping by limiting rotation around the port long axis, which enhances the stability of a port with a broad base and permits the design of a stable port with a narrow or absent base. A narrow or absent base enables the port to fit through a small incision. Implantation is further enhanced by expanding the use of the Seldinger technique including the use of dilators and/or balloons in place of blunt dissection to fashion a subcutaneous pocket for a port. In embodiments, the back of the port comprises a closeable aperture, so that the entire portacatheter, with the port and catheter attached, can be inserted over a guidewire.

26 Claims, 23 Drawing Sheets

Related U.S. Application Data filed on May 9, 2024, provisional application No. 63/563,101, filed on Mar. 8, 2024, provisional application No. 63/556,521, filed on Feb. 22, 2024.

(52) U.S. Cl.
CPC . *A61M 39/0208* (2013.01); *A61M 2039/0211* (2013.01); *A61M 2039/0223* (2013.01); *A61M 2039/0258* (2013.01); *A61M 2039/0261* (2013.01); *A61M 2039/0273* (2013.01); *A61M 2039/0276* (2013.01); *A61M 2039/0282* (2013.01); *A61M 2205/04* (2013.01)

(56) References Cited

U.S. PATENT DOCUMENTS

| | | | | |
|---|---|---|---|---|
| 11,745,003 | B2 * | 9/2023 | Drew | A61M 39/02 604/175 |
| 2004/0068233 | A1 * | 4/2004 | DiMatteo | A61M 39/0208 604/177 |
| 2005/0124980 | A1 * | 6/2005 | Sanders | A61M 39/0208 604/891.1 |
| 2006/0184142 | A1 * | 8/2006 | Schon | A61M 39/04 604/288.02 |
| 2006/0217673 | A1 * | 9/2006 | Schulze | A61M 39/0208 604/288.02 |
| 2007/0161958 | A1 * | 7/2007 | Glenn | A61M 39/0208 604/175 |
| 2007/0219510 | A1 * | 9/2007 | Zinn | A61M 39/0208 604/288.01 |
| 2008/0039820 | A1 * | 2/2008 | Sommers | A61M 39/045 604/539 |
| 2008/0249509 | A1 * | 10/2008 | Glenn | A61M 39/0208 604/539 |
| 2009/0093765 | A1 * | 4/2009 | Glenn | A61M 5/14276 604/151 |
| 2009/0204072 | A1 * | 8/2009 | Amin | A61M 39/0247 604/116 |
| 2010/0268165 | A1 * | 10/2010 | Maniar | A61M 39/0208 427/2.28 |
| 2010/0286629 | A1 * | 11/2010 | Egle | A61M 39/0208 604/288.02 |
| 2011/0311602 | A1 * | 12/2011 | Mills | A01N 37/44 514/108 |
| 2012/0078201 | A1 * | 3/2012 | Mikami | A61M 39/0208 604/288.01 |
| 2013/0041206 | A1 * | 2/2013 | Andersson | A61F 11/00 600/25 |
| 2013/0338494 | A1 * | 12/2013 | Wiley | A61M 39/0247 29/428 |
| 2015/0133738 | A1 * | 5/2015 | Foley | A61B 17/3423 600/204 |
| 2016/0235960 | A1 * | 8/2016 | Lee | A61M 39/0247 |
| 2021/0069409 | A1 * | 3/2021 | Castleberry | A61M 5/14593 |
| 2023/0025137 | A1 * | 1/2023 | Yagi | A61M 39/0208 |

* cited by examiner

FIG. 14D
FIG. 14A
FIG. 14B
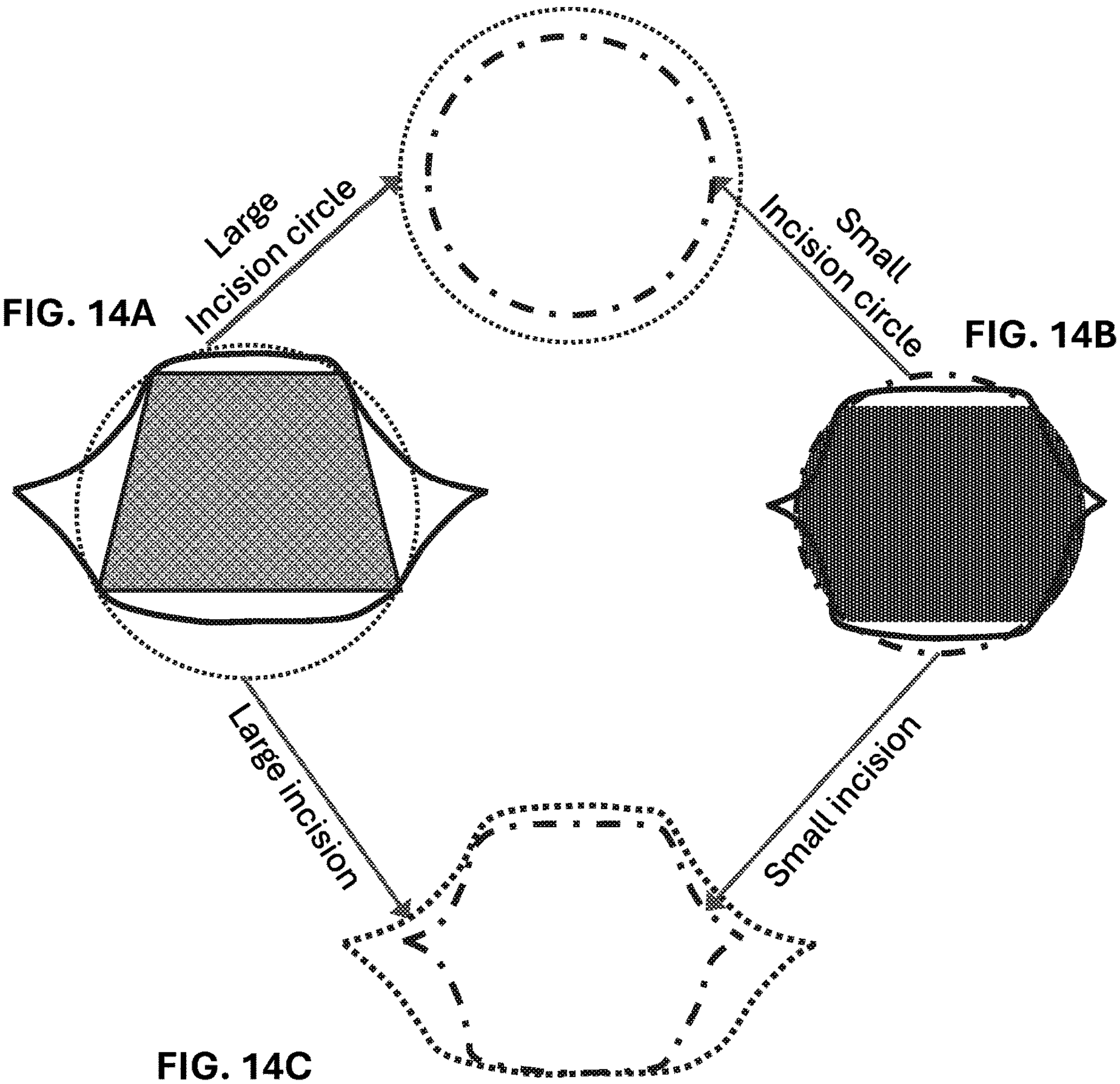
FIG. 14C
FIG. 14E
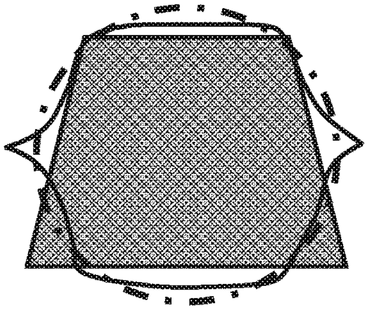

PORTACATHETERS WITH IMPROVED STABILITY THAT UTILIZE SMALL INCISIONS AND ARE EASY TO IMPLANT

CROSS-REFERENCE TO RELATED APPLICATIONS

This application claims priority from U.S. Provisional Application No. 63/556,521, filed Feb. 22, 2024, U.S. Provisional Application No. 63/563,101, filed Mar. 8, 2024, U.S. Provisional Application No. 63/644,885 filed May 9, 2024, and U.S. Provisional Application No. 63/659,158, filed Jun. 12, 2024, all of the applications identified above are incorporated herein by reference in their entirety.

BACKGROUND

Portacatheters were invented in the 1970's for repeated venous access and have become the standard of care for delivery of chemotherapy to oncology patients. At the outset, portacatheters were designed for placement by general surgeons. Over the past several decades, however, portacatheters have been increasingly placed by interventional radiologists and other specialists who perform minimally invasive procedures.

Portacatheters generally comprise two components, a port, which is delivered into a "pocket" within the subcutaneous tissues of the chest or arm through a large "port incision" and a catheter, which is delivered into a vein via a small incision. When linked together the reservoir of the port and the lumen of the catheter are connected and continuous. The catheter extends from the port through the subcutaneous tissues, then extends further via the entry vein to a central vein, typically the superior vena cava or right atrium.

The top of the port comprises a penetrable septum or "drum" that is self-sealing. If the top surface of the port is oriented correctly within the pocket, with the drum near the skin surface and roughly in a plane parallel to the skin, the port can be accessed repeatedly with a Huber needle. However, if the top of the port rotates away from the skin, which may be referred to as "flipping" in the pocket, then the port cannot be accessed, and it generally requires surgical revision. As used herein, the "stability" of a port refers specifically to resistance to flipping in the pocket.

The techniques used to place a portacatheter have not changed much since the original devices. One legacy of the original portacatheter design is the need for surgical blunt dissection to create a subcutaneous pocket into which the port is inserted. After a shallow port incision, the wound is extended a little deeper into the subcutaneous tissues, typically about 4 to 8 mm. The operator then uses Kelly clamps, a surgical blade and usually an index finger to dissect through a fascial plane to fashion a subcutaneous pocket.

Some practitioners suture the port to the chest wall to prevent the port from flipping. However, this is typically not necessary if the pocket is of the right size, large enough to accommodate the port without skin tension but small enough that the surrounding soft tissues constrain movement.

Blunt dissection requires surgical skill and judgment, and it can be time-consuming. Further, depending on the operator, pockets may be too large, which can lead to the port flipping, or too small, which can lead to skin injury. In Applicant's U.S. Ser. Nos. 63/556,521, 63/563,101, 63/644,885, and 63/659,158, alternatives to blunt dissection for portacatheter implantation were described, including the use of dilators and balloons. The embodiments described herein teach the use of balloons and dilators during portacatheter implantation.

The length of the standard incision for implantation of the portacatheter is determined by the size and shape of the port, most significantly the width of the port base. Known portacatheters comprise broad flat bases in cross-section to resist flipping in the pocket. A liability of a port with a broad base, however, is that implantation necessitates a long incision, commonly 3 centimeters or longer, which leaves a noticeable scar, and which requires time and skill to close. Narrowing the base permits a shorter port incision, but a narrow base makes an unsutured port less resistant to flipping. Thus, there is a need in the art for a stable portacatheter that does not flip in the pocket even if unsutured and that can be easily implanted through a small incision. Toward that end, herein are disclosures of embodiments of a port that may have any combination of rounded and/or planar sides, wings, and bases, all of which follow a set of novel guidelines.

Applicant's U.S. Ser. No. 63/556,521 described a port with a base that was either absent or limited to less than two radians of a roughly circular cross-section. These portacatheter designs included at least two elements: (1) the cross sections for the embodiments of the portacatheter as they were inserted into a subcutaneous position were roughly circular; and (2) there were one or more mechanisms to anchor the port in the pocket to prevent or resist rotation, wherein the anchoring mechanisms also fit within the same roughly circular cross-section as the portacatheter. Applicant's U.S. Ser. No. 63/556,521 has been incorporated by reference for the subject matter of portacatheter device descriptions and the methods of implantation of portacatheters into a patient, which can be additionally applied to portacatheters disclosed herein.

Applicant's U.S. Ser. No. 63/563,101 described the addition of wing components and/or a retention cuff to standard ports having a mostly trapezoidal cross-section. Additionally, the application taught that anchoring mechanisms could extend lateral to the core port cross-section, while providing specific guidelines, wherein the port-plus-anchoring mechanisms fit through the same incision as the port without the anchoring mechanisms. The application introduced the incision circle concept, which is also used in the invention. The cited applications here and above are incorporated by reference in their entirety based on the discussed concepts including, for example, increased port stability designs, retention cuffs, wing extensions, and anchoring mechanisms, as well as dilators and methods of implantation of portacatheter devices, which can be additionally applied to portacatheters disclosed herein.

In addition to fixed structures, invention embodiments include wing extension structures that can be expanded mechanically or are self-expanding. The primary design guideline for an expanding wing retention system is that the port long-axis profile at the time of insertion fits through the same incision circle as the port without the expanding retention system. Once expanded, the resulting port may assume any shape. Embodiments of the invention result in a broad range of structures that primarily restrict rotation around the long axis.

Regarding mechanically-expanding wing extension structures, FIG. 2 of Applicant's U.S. Ser. No. 18/439,985 is incorporated by reference in its entirety based on concepts including for example, the mechanical system to expand the wings of the portacatheter and methods of implanting and removing catheters, which can be applied to embodiments of the portacatheter, such as the Seldinger embodiments, disclosed herein.

Regarding self-expanding wing extension structures, the wings could be Nitinol, plastic, metal, alloy, or any other material that could flange outward after removal of a constraining membrane or movement of another physical mechanism. An example would be if a port were inserted through a peel-away sheath. Once the port is positioned favorably in the subcutaneous tissues, the peel-away sheath would be removed, and the self-expanding wings would flange outward, forward, backward, and could expand beyond the cross-section of the portacatheter.

An observation underlying the invention is that ports can be designed to more fully utilize the port incision. At the time of insertion through the skin, known ports comprise cross-sections that do not conform to the shape of the incision, creating portions of the incision where there is tension and portions where there is laxity. On the other hand, inventive embodiments include ports that more uniformly and smoothly fit through the port incision. Such inventive port embodiments comprise extensions that improve stability, including lateral extensions that create ports with sides that are wider than the base. This permits the implantation of inventive ports through shorter incisions than known ports with identical functional cores, as is demonstrated for example in FIGS. 12 and 13.

There is a need for portacatheters that are stable, are designed to fit through a small incision, and can be implanted more rapidly and with greater ease. Embodiments of the invention are designed to resist flipping in the pocket even without a broad flat base, which allows designs that have either a narrow flat base or no flat base. Such novel designs reduce or even minimize the port incision, shortening the surgical scar. Embodiments of the invention also enhance speed and ease of insertion by providing a port profile more amenable to the use of dilators, rather than blunt dissection, for pocket creation. In a preferred embodiment, there is a closeable aperture at the back of the port, which allows the entire device to be inserted via a guidewire using the Seldinger technique.

BRIEF DESCRIPTION OF THE DRAWINGS

FIG. 3A represents an implanted device having a stabilizer bar configured to the sealed back aperture. FIG. 3B illustrates a guidewire through the port lumen and the catheter lumen.

FIG. 4A provides an example of a collinear port and catheter long axes. FIG. 4B provides an example of a non-collinear port and catheter long axes and having an angle theta.

FIG. 6A, the base is wider than the top. FIG. 6B, the base is the same size as the top. FIG. 6C, the base is narrower than the top. FIG. 6D, the base is a point, and the shape of the geometric core port is an inverted cone. The dotted line is the superimposed drawing of FIG. 6A.

FIG. 9A, FIG. 9B, and FIG. 9C represent a Vygon Polysite 2000. FIG. 9D, FIG. 9E, and FIG. 9F represent a Bard PowerPort Implantable Port. The rectangles of FIG. 9C and FIG. 9F represent the base plane square for each port.

FIG. 10A, FIG. 10B, and FIG. 10C; perspective view: FIG. 10D, FIG. 10E, and FIG. 10F). The outlines of the core port are depicted in FIG. 10B and FIG. 10E (black outline) using different perspectives and are overlayed on the matching perspectives for images of FIG. 10C and FIG. 10F, respectively. The checkered portions of FIG. 10C represent lateral extensions.

FIG. 11A demonstrates the incision circle having a cross-section of a trapezoidal core port set within the incision circle. FIG. 11B demonstrates various port devices having variable base widths set within their respective incision circle having the identified diameter. The specific values are in millimeter (mm) and are for purposes of illustration and are not limiting.

FIG. 12A is a photograph of a partially inserted AngioDynamics port into an incision. FIG. 12B, the schematic represents a port insertion in the approximated incision shape (black filled space) to simulate the photograph in FIG. 12A. FIG. 12C is a representation of an embodiment port insertion into an incision. Incision circles (dotted line) for each device are depicted in FIG. 12B and FIG. 12C. Values are in mm and are provided as non-limiting approximations for purposes of illustration.

FIG. 13A demonstrates a functional core port (dashed line cylinder) within a geometric core port (solid line) and entering a representative incision. FIG. 13B demonstrates the identical functional core port (dashed line), but within an embodiment port (solid line drawing of device). Incision length values are approximations for purposes of illustration and are not limiting.

FIG. 14A, FIG. 14B, FIG. 14C, FIG. 14D, and FIG. 14E demonstrate ports set within their respective incision circle and respective incision. FIG. 14A shows a port cross-section having a trapezoidal shape (filled in shape) is shown to be set within an incision (solid line) and within an incision circle (dotted line). FIG. 14B, an embodiment port is shown to be set within an incision (solid line) and within an incision circle (dashed and dotted line). The incisions and the incision circles are overlayed in FIG. 14C and FIG. 14D, respectively. FIG. 14E, the device cross-section of FIG. 14A is set within the incision and incision circle of FIG. 14B.

FIG. 15A shows a trapezoidal port cross-section is set in its corresponding incision shape (long dash line) and incision circle (dotted line). FIG. 15B, the device has the same core shape and size as the device in FIG. 15A, but with the addition of lateral extensions (black rectangles and rounded darker shading) of an embodiment of a Structural Invention set within the same size incision circle and incision shape as in FIG. 15A.

FIG. 16A is an image of an AngioDynamics Smart Port CT Mini as viewed from the top. FIG. 16B, the base extensions of the port in FIG. 16A are highlighted (checkerboard). FIG. 16C, a base square and, in this case, rectangle is outlined (gray rectangle) and superimposed onto the image of the device in FIG. 16A.

FIG. 17A shows a core port represented as an upright truncated cone. FIG. 17B demonstrates the orientation of the sidewall rectangles, the dimension labels for the length of the sidewall rectangle, the height of the sidewall rectangle, and the base plane. FIG. 17C demonstrates an embodiment of the invention illustrating the lateral sidewall extensions.

FIG. 18A shows a device having rectangular-based sidewalls, but the height of the lateral sidewall rectangle is minimal. The sidewall rectangles and dimension labels for the length of the sidewall rectangles and the height of the sidewall rectangle are shown. FIG. 18B, the lateral sidewalls extend beyond the width of the base but are not contiguous with the base plane.

FIG. 20A illustrates an AngioDynamics Smart Port CT Mini with the corresponding core port overlay (dashed lines). FIG. 20B is a top view of the same port as in FIG. 20A with a drawn overlay (black circle) identifying the core port base circle. FIG. 20C illustrates the top view as in in FIG. 20B and highlights the base extensions (checkerboard filled in space) of the device in FIG. 20A. FIG. 20D illustrates an embodiment of the base component of the Structural Invention concept illustrating the base extensions (dotted filled in space). FIG. 20E is a rendering of a port embodiment having the same base extension (dotted filled in space) as shown in FIG. 20D.

FIG. 24A, a simple dilator comprises a tapered front, a hub at the back with a handle, and a uniform cylindrical shaft between them having diameter (D). FIG. 24B is the top aspect view of an example of a complex dilator comprising at least 3 shaft segments, a front segment (S1) with diameter D1 and length L1, a back segment (S2) with diameter D2 and length L2, and a tapering transition segment (TS) with a length LTS connecting segments S1 and S2. The lumen has a diameter (DL).

FIG. 25A demonstrates a lateral aspect view of the complex dilator. FIG. 25B demonstrates a top aspect view of the complex dilator embodiment having sharp edges at the TS. FIG. 25C shows various cross-sections of the device at the provided cross-sectional cross-line through the device.

FIG. 26A, the first dilator has a uniform shaft having diameter D. FIG. 26B, the second dilator comprises a S1 having diameter D1 and a larger S2 segment having diameter D2, with a transition segment, TS, bridging the S1 and S2 segments via a taper. FIG. 26C, the third dilator is like the second dilator (FIG. 26B), but the S2 has a larger diameter D2 than in the device in FIG. 26B.

FIG. 27A represents the lateral aspect view. FIG. 27C represents the top aspect view. FIG. 27B represents the cross section view. The location of the cross-section is identified by the vertical dashed line. The sharpish leading edges are identified by the solid arrows. The handle attached to the hub is identified by the dotted line arrows.

FIG. 28A shows the ballon uninflated having diameter D2U. FIG. 28B shows the balloon inflated having a larger diameter D2I.

FIG. 29A, the illustrations demonstrate when the balloon is not inflated. The top drawing illustrates the side view the device having a blunted needle, the middle drawing illustrates the top view of the device with a narrow semi-sharp front, and the bottom drawing illustrates the top view with a broad semi-sharp front. FIG. 29B, the top, middle, and bottom illustrations demonstrate when the balloon is inflated for each of the top, middle, and bottom depictions in FIG. 29A, respectively.

FIG. 30A illustrates a port having a top width, a sidewall width, and a base width. FIG. 30B, the port example has a sidewall width (black curved line). The core port (black dashed outline) of FIG. 30A is overlayed on the device and the outline of the sidewall extensions (black lines) are shown. FIG. 30C is the same device as depicted in FIG. 30B as viewed from a different perspective. Additional outlines of the device (black lines) are shown. Each illustration identifies the top width (dotted line arrows), the sidewall width (dashed line arrows), and the base width (solid line arrows).

FIG. 31A illustrates a port having a top width, a sidewall width, and a base width. FIG. 31B is an example of a port having a sidewall extension continuous with wings. The core port (black dashed outline) of FIG. 31A is overlayed on the device. FIG. 31C is the same device as depicted in FIG. 31B but is viewed from a different perspective. Each illustration identifies the top width (dotted line arrows), the sidewall width (dashed line arrows), and the base width (solid line arrows).

32B, and FIG. 32C. FIG. 32A and FIG. 32D show the same device from different views. FIG. 32B and FIG. 32E show the same device from different views. FIG. 32C and FIG. 32F show the same device from different views. FIG. 32C, the potential height of the base extension (dimension arrows with dotted lines) as determined in the height axis.

FIG. 33A, an AngioDynamics Smart Port CT Mini is viewed from the back and has a drum diameter of about 10.5 mm and base width of about 17 mm. The incision circle (black circle surrounding the port) diameter is about 20 mm. FIG. 33B, a cross-section of an embodiment has a similar top width and base width as the device depicted in FIG. 33A. FIG. 33C, the port base has been narrowed, for example, from about 17 mm to about 14 mm and the incision circle (circle having a dashed and dotted line) is depicted. All dimensions are in millimeter (mm).

FIG. 34A shows the Bard M.R.I. Ultra SLIMPORT. FIG. 34B is a modified version of the port as depicted in FIG. 34A, but with the corresponding port, and with the addition of lateral extensions superimposed on the image of FIG. 34A. FIG. 34C, the port base (superimposed cylinder) has been narrowed from the device depicted in FIG. 34B.

FIG. 35A illustrates another example of the Seldinger Portacatheter embodiment having lateral extensions, wing extensions, and base extensions. FIG. 35B illustrates base extensions that taper and have a height (dotted line brace) less than or near the mid height of the port device.

FIG. 36A, the port has a top of about 12 mm, a drum of about 8 mm, and base of about 15 mm, while having an incision circle (black outer circle) of about 18.5 mm. FIG. 36B, the port has the same top as depicted in FIG. 36A, a base of about 12 mm, and an incision circle (dot-dash middle circle) of about 15 mm. FIG. 36C, the port has the same top as depicted in FIG. 36A, a rounded base, and an incision circle (dotted inner circle) of about 13 mm. All dimensions are in millimeters (mm).

DEFINITIONS

1. A "portacatheter" is a device comprising a port segment and a catheter segment extending from it. It may also be referred to as a "port-a-cath," and there are various other generic and commercial names.

2. The "port" segment is the part of a portacatheter that comprises a permeable septum or drum through which a needle may be inserted, a luminal chamber or reservoir into which a needle may be inserted, an aperture to communicate with the lumen of a catheter, and impermeable port sides and a port base that enclose the reservoir. The port is inserted into the subcutaneous tissues via a "port incision."

3. The "catheter" segment is the tubular part of the device that extends from the port, through the subcutaneous tissues, and into a location such as the venous system. The catheter has a lumen with holes at either end, one of which communicates with the reservoir or luminal chamber of the port.

4. A portacatheter "drum" or "septum" refers to the usually circular permeable structure located in approximately the top plane of the port, which is where a Huber needle is inserted to access the port.

5. The "luminal chamber" or "reservoir" is the internal region of the port that receives the needle and communicates with the lumen of the catheter via an aperture generally at the front of the port.

6. The "long axis of a port" or "major axis of a port" refers to an imaginary line within the plane of the port base that, when a port is viewed from above, crosses the center of the drum and the point of connection between the catheter and the port.

Figure 4A:
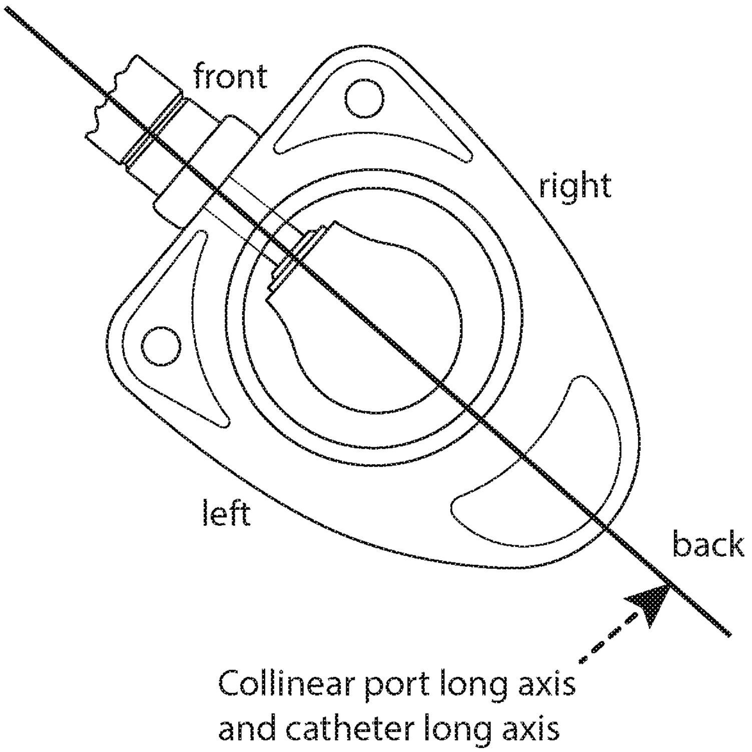
FIG. 4A and FIG. 4B are examples of ports demonstrating catheter long axes.
Figure 4B:
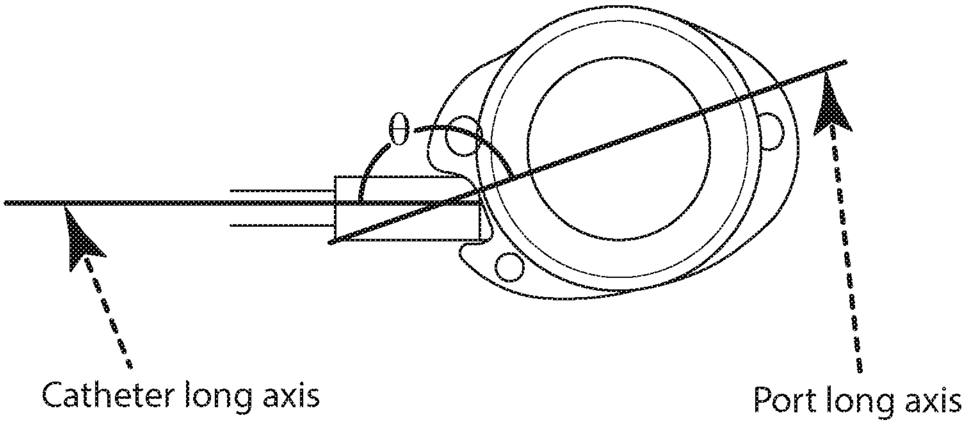

7. The "long axis of the catheter" is an imaginary line within the plane of the port base that is parallel to the luminal path of the catheter as it extends from the port. In many but not all portacatheters, the long axis of a port and the long axis of a catheter are roughly parallel. FIG. 4 demonstrates the long axes of two known ports. FIG. 4A demonstrates parallel axes and FIG. 4B demonstrates non-parallel axes.

8. Port "left" and "right" are defined as viewed from the back of the port.

9. The "front" of the port is defined as the aspect to which the catheter attaches. The front portion may be referred to as "distal." In the case of a venous portacatheter, it is the aspect that projects in the direction of the venous system.

10. The "back" of the port is the aspect opposite the front and may be referred to as "proximal."

11. The "length" of a port is defined as the maximum distance, including the base, from the front of the port (distal) to the back of the port (proximal) along the long axis dimension.

12. Port "stability" in this document refers specifically to resistance from flipping, which typically is caused by rotation around the long axis of the port.

13. A "cross-section" of the port or "port cross-section" refers to imaginary planes through the port that are orthogonal to the port long axis. A port is assumed to be inserted into a subcutaneous pocket along the long axis of the port in a direction roughly perpendicular to the incision. Therefore, the port cross-sections comprise the planar shapes that pass through the incision.

14. The port "silhouette" is defined as the aggregate of all port cross sections superimposed onto a planar surface. In other terms, a long-axis silhouette comprises all the cross sections along the long axis that must pass through the incision during implantation. There are also minor axis and height axis silhouettes produced by a composite of all the cross-sections created along their respective axes.

15. The "minor axis" of a port is orthogonal to the major axis and within the plane of the port base. Measurements along the minor axis may be referred to as "transverse." See FIG. 5.

16. The "height" axis of a port is an imaginary line through the center of the drum and perpendicular to the base and/or top. The height of a port is the distance between the top and base along the height axis. See FIG. 5.

17. The "mid-sagittal plane" of the port is defined as the plane containing the long axis and height axis, bisecting the port into right and left halves.

18. A port consists of a "top," a "base" and a "side" or "sides." For any port, the top comprises the drum and any surrounding rim roughly coplanar with the drum. The base refers to the aspect opposite the top. The side or sides refers to the port surface between the top and base. For this document, the sides are defined to range from 2 mm above the base to 2 mm below the top.

Figure 6B:
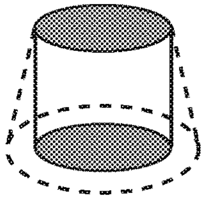
Figure 6C:
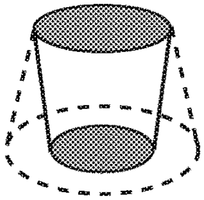
Figure 7A:
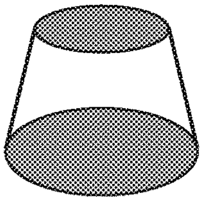
FIG. 7A, FIG. 7B, FIG. 7C, and FIG. 7D are examples of various core port shapes as described for FIGS. 6A-6D.
Figure 7B:
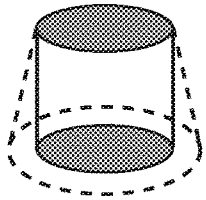

Ports can be characterized as a "core port" plus "extensions," terms which are defined as follows:

19. The "functional core port" represents a cylindrical shape with a top corresponding to the top of the port, with a base that is centered under the top and the same size as the top, and with sides extending from the top to the base. An example of a functional core port is demonstrated by the solid lines in FIG. 6B and FIG. 7B. In general, the functional core port comprises the drum, reservoir, and an aperture for communication with the lumen of the catheter.

Figure 6A:
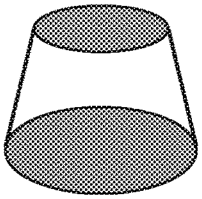
FIG. 6A, FIG. 6B, FIG. 6C, and FIG. 6D provide examples of geometric core ports.
Figure 7C:
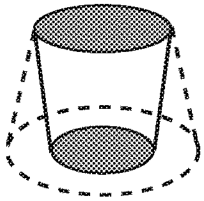

20. The "geometric core port" represents a geometric shape related to but distinct from the functional core port. Herein, the term "core port," absent a qualifier like functional or geometric, or the term "core," absent the word port, refers to the geometric core port. The geometric core port shape may be used to characterize the underlying shape of any port. While a functional core port is always a cylinder (FIGS. 6B and 7B), a geometric core port may be various shapes, as shown in FIGS. 6A, B, C and D and in FIGS. 7A, B, C and D. The drawings of FIGS. 7E, F, G, and H represent inventive port embodiments associated with the core ports of FIGS. 7A, B, C and D.

21. The geometric "core port top," "core port top surface," or "top surface" is a flat circle at the upper margin of a core port comprising a drum and a surrounding rim.

Figure 6D:
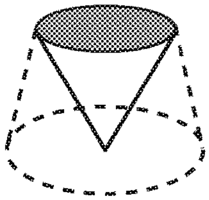
Figure 7D:
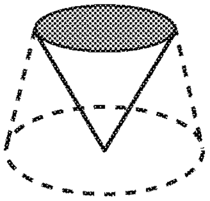
Figure 7E:
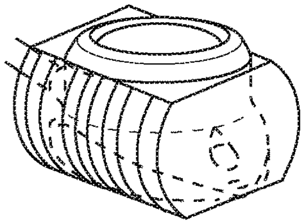
FIG. 7E, FIG. 7F, FIG. 7G, and FIG. 7H are representative embodiments of portacatheter devices utilizing the core port shapes of FIGS. 7A-7D, respectively.
Figure 7F:
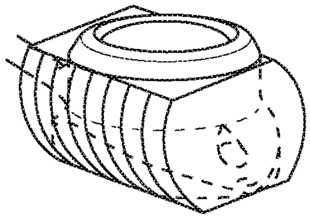
Figure 7G:
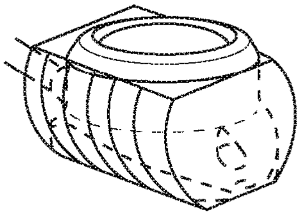

22. The geometric "core port base circle" or "core port base" is defined as a flat circle at the lower margin of a core port that is centered under the drum. As shown in FIG. 6D and FIG. 7D, the core port base may also be a point.

23. The geometric "core port side" or "core port sides" is defined as the conical surface extending from the core port top to the core port base. See for example, FIG. 5, wherein slanted lines connecting the bottom circle to the top circle represent the side or sides of the core port.

24. A port "top extension" is any structure extending outward from the core top comprising a planar surface that is roughly (within 2 mm height) co-planar with the top. An example of a top extension is present in the Bard PowerPort (BD Catalog #SKU: 1759601, GTIN: 00801741026867) portacatheter shown in FIG. 8A.

25. A port "base extension" is any structure extending outward from the base comprising a planar surface that is roughly co-planar (within 2 mm height) with the base. Known ports often comprise base extensions, primarily to widen the base for stability. Examples of known base extensions are shown in FIG. 9.

26. A port "lateral extension" is any structure extending laterally from the right and/or left sides of the port. For example, a lateral extension is demonstrated by the shaded portions of the AngioDynamics Smart Port CT Mini (AngioDynamics Catalog #H787CT50PTBDVI0) in FIG. 10C.

Known ports comprise a variety of shapes and sizes. The following definitions identify the underlying geometric core ports of known ports.

Figure 8A:
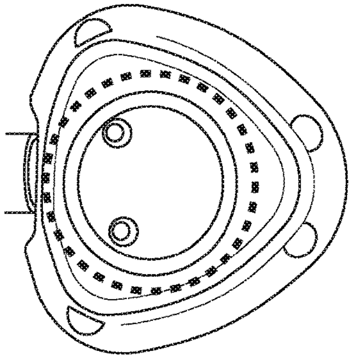
FIG. 8A, FIG. 8B, and FIG. 8C provide examples of tops for two ports, a Bard PowerPort Implantable Port (BD Catalog #SKU: 1759601, GTIN: 00801741026867) (FIG. 8A and FIG. 8B) and a Vygon Polysite 2000 (FIG. 8C).
Figure 8B:
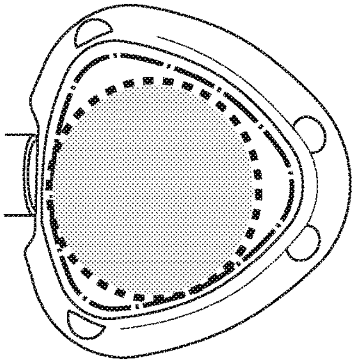
Figure 8C:
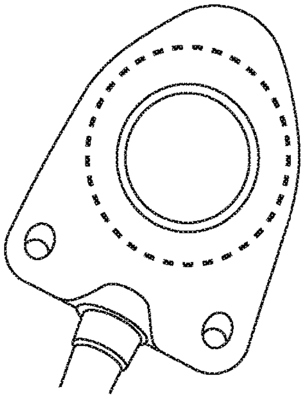
Figure 9A:
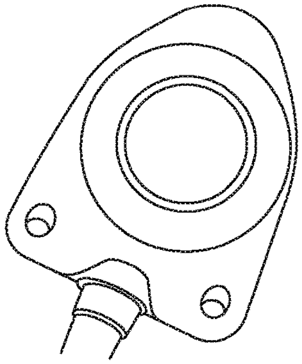
FIG. 9A, FIG. 9B, FIG. 9C, FIG. 9D, FIG. 9E, and FIG. 9F provide examples of bases of ports and their base extensions.
Figure 9B:
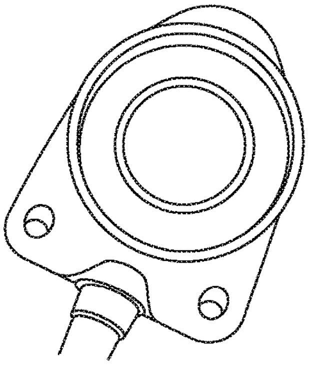
Figure 9C:
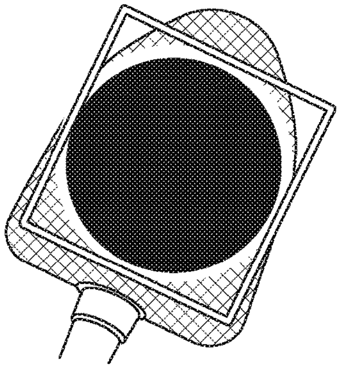
Figure 9D:
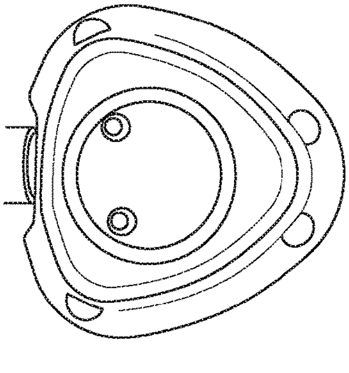
Figure 9E:
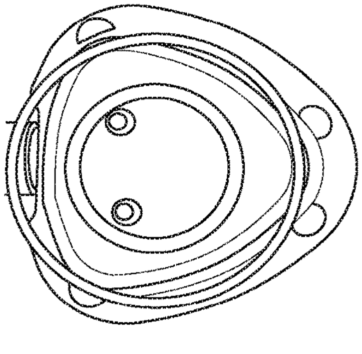
Figure 9F:
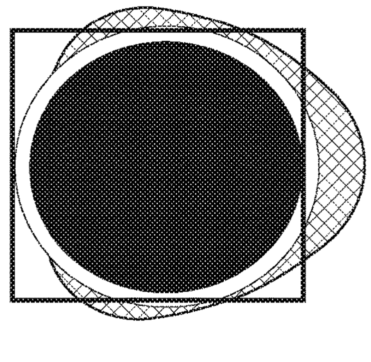

27. The core port top of a known port comprises the drum and surrounding rim of the known port. An outer margin of the core port top is defined by a juncture at which there is a "primary descent" from the top. The "primary descent" is defined as a monotonic downward progression from the approximate level of the drum to the level of the base. If the drum of a known port is surrounded by a triangular shape or any other shape that is roughly coplanar with the drum (angle of descent less than about 20 degrees from the drum), then the outer rim is defined as a circle centered around the drum, contained entirely within the triangular or other shape, and intersecting at least one side of the triangular or other shape. An example of a core port top circle fitted within a triangular shape portacatheter top is shown in FIGS. 8A and 8B. An example of a core port top circle fitted within a circular portacatheter top is shown in FIG. 8C.

28. The "core port base circle" or "core port base" of a known port is defined as a flat circle that is centered under the drum and which, other than a possible small depression (arc less than or equal to 60 degrees) at a segment containing the attachment origin of the catheter, is contained entirely within a continuously solid portion of the port base. Some ports comprise combined base and top extensions, for example, the Bard PowerPort (BD Catalog #SKU: 1759601, GTIN: 00801741026867) in FIGS. 8A and 8B.

Figure 19:
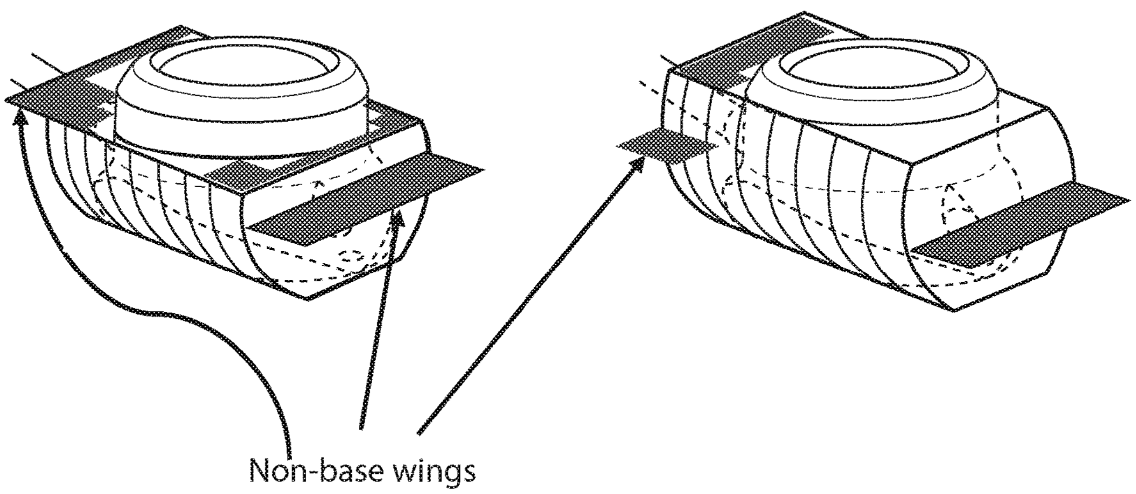
FIG. 19 demonstrates embodiments of wings (non-base wings) of the Structural Invention concept extending in front of or behind the port (arrows).

29. A port "non-base wing extension," or "wing extensions," or "wings" is defined as a non-base outward extension from the surface of the core port. As used in the current document, wings primarily refer to surfaces in front of and behind the core port. A wing may be completely or only partially planar. It may also comprise rounded portions. Wings may comprise relatively sharp edges, points, or barbs. A wing may extend in any rotational orientation from the core port, such as horizontal, vertical, or any angle in between horizontal or vertical. The number of wings may vary and may be asymmetric. FIG. 19 demonstrates wings extending in front of and behind selected port embodiments. A wing may comprise prepositioned holes for sutures.

As will be elucidated in the Discussion, known ports comprise geometric cores plus known extensions, while inventive embodiments comprise geometric cores plus novel inventive extensions.

30. Across all cross-sections of the port, width is measured as follows:

a. The "base width" is the greatest width at the level of the base.

b. The "top width" is the greatest width at the level of the top.

c. The "side width" is the greatest width at any level of the side.

In other terms, the base width is the width of the long-axis silhouette at the level of the base, the top width is the width of the long-axis silhouette at the level of the top, and the side width is the greatest width of the long-axis silhouette side.

31. The overall "port width" is defined as the largest of the base, top, and side widths.

32. The expression "the port is wider at the sides than at the top and base" is defined to mean that the side width is greater than the top width and the base width.

33. Across all cross-sections of the port, "lateral extent" is defined as follows:

a. The "base lateral extent" is the greatest lateral distance from the mid-sagittal plane at the level of the base.

b. The "top lateral extent" is the greatest lateral distance from the mid-sagittal plane at the level of the top.

c. The "side lateral extent" is the greatest lateral distance from the mid-sagittal plane at any level of the side.

34. The expression "the port sides and/or sidewalls extend laterally beyond the top and base" is defined to mean that the side lateral extent is greater than the top lateral extent and the base lateral extent.

35. A "broad base" or a "broad flat base" is defined as the base width being greater than the top and side width.

36. The "incision circle" of a port is a circle that has a circumference large enough to contain any cross-section of the geometric core port. In other words, the incision circle comprises a circle that touches all 4 angles of a core port trapezoidal cross-section.

In actual surgery, as a port is inserted, the port incision is not a perfect circle. The relationship between an incision circle and a port incision approximating real life surgery is demonstrated in FIGS. 12, 13, 14, and 15.

The incision circle concept is used in this document for at least 2 purposes: (1) to rank order the incision necessary to deliver a port; and (2) to define embodiments of the Structural Invention. The concept of an incision circle is demonstrated in FIG. 11.

A guideline of the lateral extension component of the Structural Invention is that the core port, including lateral extensions, is wider at the side than at the top or base. While this may be achieved through adding a variety of lateral extensions, preferred embodiments include ports wherein this sides-wider-than-base-and-top condition exists for some length over the lateral aspects of the port. To specify this embodiment of the invention, this document includes the following concepts and definitions:

37. The "lateral sidewall planes" are imaginary flat planes tangential to the core port defined by containing only the lateral-most lines of the core port sides.

38. The "lateral sidewall rectangles" are imaginary subsets of the sidewall planes of the core port wherein:
  a. the "length axis of the sidewall rectangle", which is used to measure the length of the sidewall rectangle, is in the direction of the port front to the port back;
  b. the "height axis of the sidewall rectangle", which is used to measure the height of the sidewall rectangle, is within the plane of the lateral sidewall rectangle and orthogonal to the length.

Each of the height, length and position aspects of the lateral sidewall rectangles may vary. FIG. 17 and FIG. 18 illustrate sidewall rectangle length and height.

As defined above, port "sidewalls" differ from port "side" or "sides." The port side or sides refers to the surface structure between a port top and base. On the other hand, sidewalls refer specifically to only the lateral-most portion of an embodiment side. The term sidewall is used in this document to explicate a particular embodiment of the lateral extension component of the Structural Invention.

The lateral sidewalls of the port embodiments project outward from the lateral sidewall rectangles to form shapes that make the port stable in the pocket. FIG. 17 and FIG. 18 demonstrate 2 examples of lateral sidewall rectangles and corresponding lateral sidewalls of the invention.

Although a rectangle is used as the shape from which a lateral sidewall extends, any planar shape could also be used. For example, the sidewall could extend from a parallelogram, a triangle, a circle, or any other planar shape.

39. A "base plane" is defined as the plane of a port base, having major and minor axes corresponding to the port major and minor axes. In embodiments of the port of the invention, the base of the port may be entirely round in cross-section, rather than containing a flat segment, in which case the base plane refers to a plane parallel to the drum and tangential to the rounded base.

Figure 5:
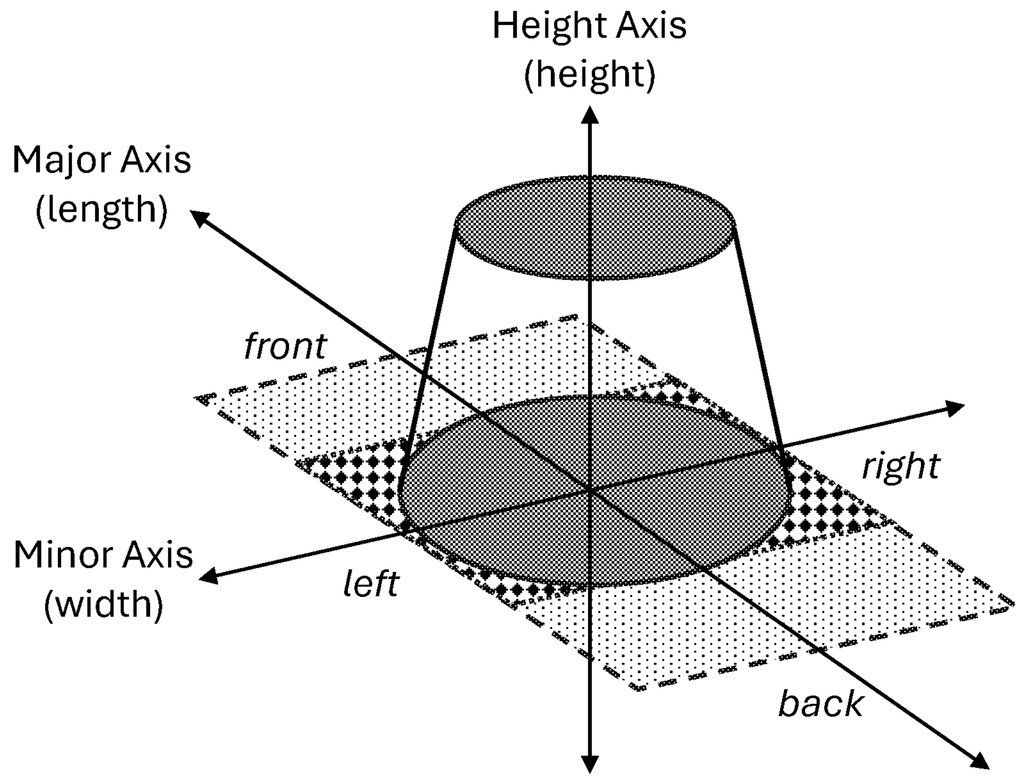
FIG. 5 is a diagram of a core port (conical shape) with a base plane square (checkerboard fill) and a base plane rectangle (dot fill). The three axes are major for length, minor for width, and height for height.

40. The "core base plane square" is defined as a square subset of the base plane, wherein the sides of the square run parallel to both port axes (major and minor), and each side of the square intersects with the core base at only 1 point. The core base plane square is therefore the smallest square that will encompass the core port base. An example of a core base plane square is shown in FIG. 5.

41. A "base plane rectangle" is defined as a rectangular subset of the base plane, wherein the base plane rectangle entirely encompasses the base plane square. The length of the base plane rectangle is measured along the port major axis, and the width of the base plane rectangle is measured along the minor axis, as is shown in FIG. 5. The base plane rectangle width is the same as the base plane square width. The base plane rectangle extends both in front of and behind the base plane square by at least 2 mm.

Figure 32A:
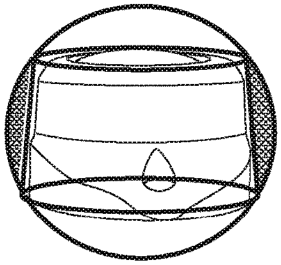
FIG. 32A, FIG. 32B, FIG. 32C, FIG. 32D, FIG. 32E, and FIG. 32F demonstrate various embodiments of the lateral extension, base extensions, and wing extension components of the Structural Invention concept. The incision circle (black circle) is drawn around the devices in FIG. 32A, FIG.
Figure 32B:
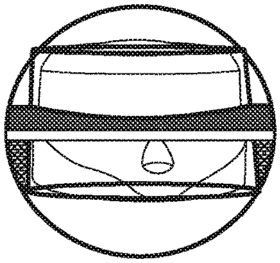
Figure 32C:
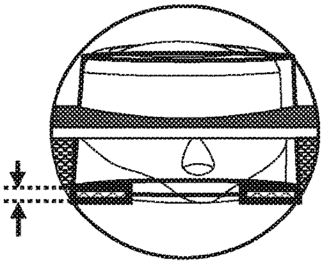
Figure 32D:
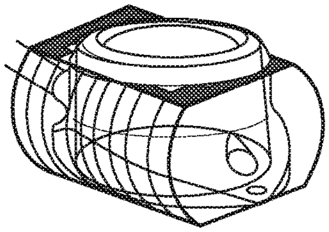
Figure 32E:
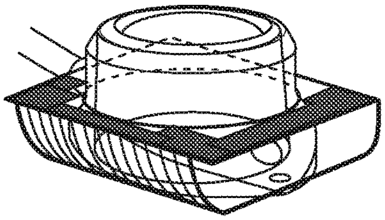
Figure 32F:
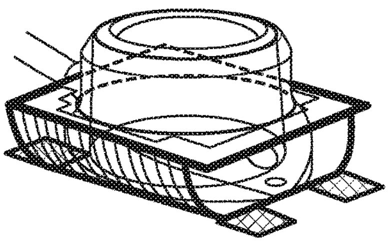

42. The "height of a base plane extension" refers to the distance from the base of the base extension to the top of the base extension and is measured in the direction parallel to the height axis of the port. Illustrations of base height are shown in FIG. 32C and FIG. 35B.

43. Port "flipping" refers to a complication of a porta-catheter, wherein the port turns sideways or upside down. For a port with a circular cross section, the equivalent complication is rotation of the port around the long axis, so that the drum has moved away from being parallel to the skin and is not accessible for percutaneous puncture.

44. The term "roughly circular," which is a term applied herein to both ports and dilators, includes shapes that are not perfectly circular but create an overall rounded contour, such as an ovoid shape. Further, a polygonal approximation of a circle, such as a hexagon, heptagon, octagon, nonagon, decagon, dodecagon, and so on, would also be within the meaning of roughly circular. In reference to a port cross-section or silhouette, because the top comprises a generally flat drum and rim, the designation of roughly circular applies to the circumference of the port other than the flat top. In addition to the flat drum and rim at the top of a port, a roughly circular port silhouette may also include a flat base segment in cross-section of up to 2 radians in length.

45. The "length of a port pocket" refers to the distance from the port incision to the furthest limit of the pocket. If a port is inserted from a caudal incision into a more cranial position, the length of the pocket refers to the distance between the incision and the cranial limit of the pocket. If a port is inserted from a cranial incision into a more caudal position, the length of the pocket refers to the distance between the incision and the caudal limit of the pocket.

46. The "width of a port pocket" refers to the distance from the lateral limit of the pocket to the medial limit.

47. A "simple dilator" is defined as a catheter with a central lumen (L) for guidewire access, wherein the dilator distal aspect has a tapered conical shape with a pointed tip, the dilator mid-portion, or shaft (S), is a long cylinder of a uniform composition having a uniform cross-sectional diameter (D), and the proximal end is a short hub of a diameter or diameters typically larger than that of the shaft. A dilator of this sort is passed over a guidewire. See FIG. 24A for an example.

48. The "long axis" of a dilator is defined as an imaginary line that is collinear with the catheter lumen, i.e., wire guide.

49. The "cross-sections" of a dilator is defined as imaginary planes orthogonal to the long axis.

50. A "complex dilator" is defined as a catheter with a central lumen (L) for a guidewire, wherein the dilator comprises at least 2 distinct segments of different diameters and/or shapes.

Figure 23:
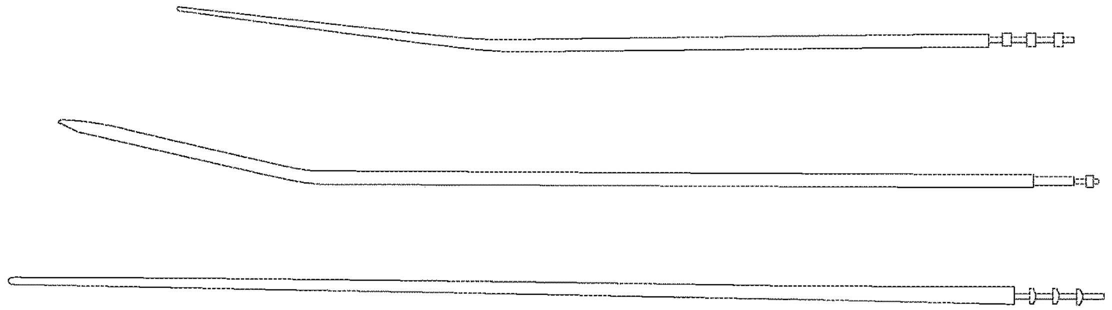
FIG. 23 demonstrates tunnelers or trocars.

51. A "tunneler" is defined as a device used to burrow through tissues for the purpose of creating a path through which a catheter may be advanced. Unlike a dilator, the tunneler is not passed over a pre-existing guidewire. However, a tunneler may or may not have a central lumen. Although there are other mechanisms to achieve wire passage, tunnelers with a central lumen are used for the purpose of advancing a guidewire after tunnelling between 2 skin incisions. Examples of tunnelers are shown in FIG. 23.

52. The "height" of a dilator refers to the cross-section axis perpendicular to the skin at the time of insertion, which is typically in this document is the shorter diameter if the dilator cross-section is non-circular.

53. The "width" of a dilator refers to the cross-section axis parallel to the skin at the time of insertion, which is typically in this document is the longer diameter if the dilator cross-section is non-circular.

54. The "hub" of the dilator is defined as the back end, as for example pictured in FIG. 24.

55. The shaft of a complex dilator may be divided into 3 segments. The distal portion will be referred to as Segment 1 (S1), which has length L1 and diameter D1. The proximal portion will be referred to as Segment 2 (S2), which has length L2 and diameter D2. See FIG. 24B. The "transition segment" (TS) is the dilator portion between S1 and S2.

56. A "dissector" or "dissector dilator" is a special dilator that may function primarily as a device to dissect a plane for subsequent dilatation. The dissector dilator cross-section has a higher width to height ratio (i.e. it is flatter) than other dilators, and it may have a sharpish leading edge that extends along more of the lateral margins of the dissector device, for example along the margins of S2 as well as the transition segment. A non-limiting example of such a device is shown in FIG. 27.

57. The term "about" is to allow for the tolerance of manufacturing within plus or minus (±) of 2%, 3%, 5%, 8%, or 10% for the provided value.

58. The term "mm" refers to millimeter, and "F" refers to the French catheter scale that is used for measuring the diameters of medical catheters.

59. The Seldinger technique comprises the use of a guidewire to deliver a catheter through the skin into a pre-selected structure, such as a vein. In this document, the term Seldinger and "over-the-wire" may be used interchangeably.

SUMMARY OF THE INVENTION

Embodiments herein comprise guidelines for a novel portacatheter system.

Figure 1:
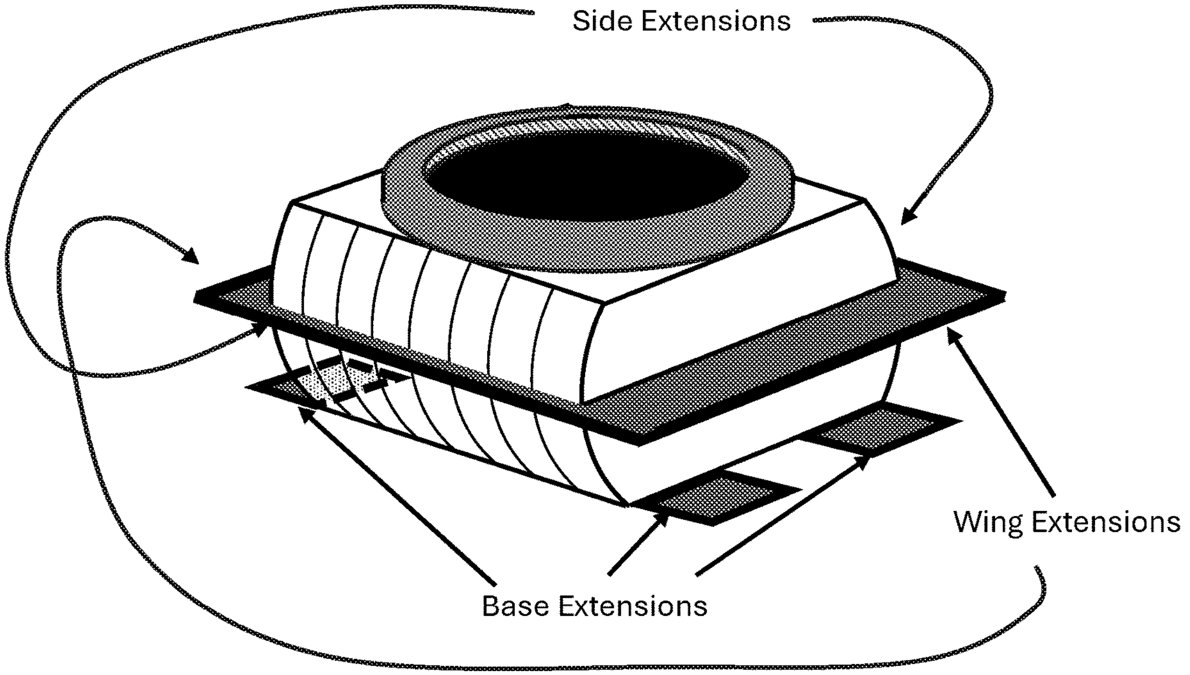
FIG. 1 is an embodiment of the Structural Invention portacatheter.

Selected embodiments comprise structures that extend from a core port to provide stability. This concept will be referred to as the "Structural Invention." An embodiment of the Structural Invention is shown in FIG. 1.

Figure 2:
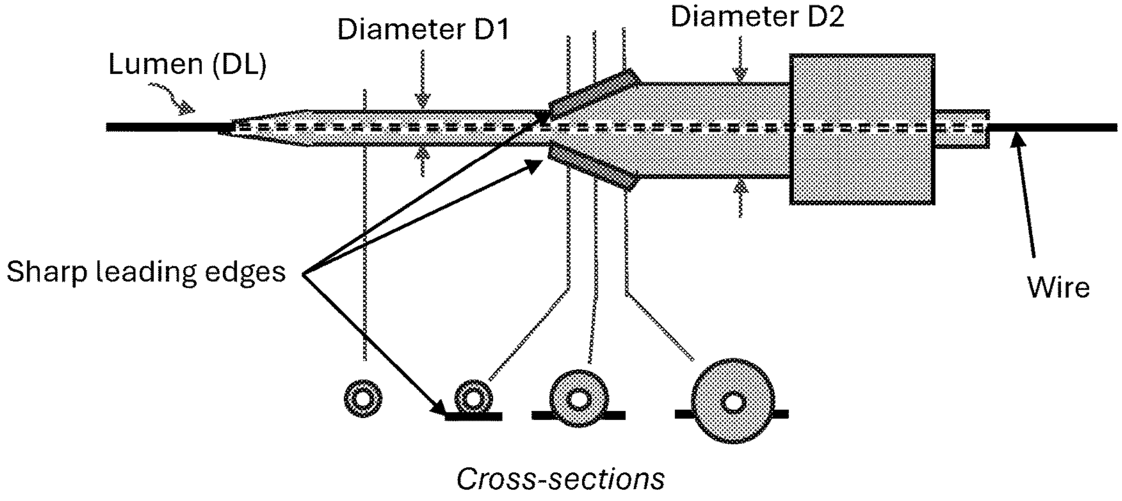
FIG. 2 is an embodiment of the Dilator Invention with a transitional segment having sharpish leading edges. The top image is a view of the top aspect. The bottom images are cross-sections from the identified sectional lines.

Other embodiments comprise novel dilators and balloons that may be used to create a subcutaneous pocket for a port. This concept will be referred to as the "Dilator Invention" and incorporates by reference Applicant's U.S. Ser. No. 63/659,158 in its entirety for the concepts regarding the use of a dilator for the implantation of catheters or portacatheters disclosed herein or incorporated by reference. An embodiment of the invention is shown in FIG. 2.

Other embodiments comprise a back-of-the-port aperture and associated changes to enable a portacatheter to be inserted over a guidewire. This concept will be referred to as the "Seldinger Portacatheter Invention." An embodiment of the invention is shown in FIG. 3.

The invention encompasses a stable portacatheter that can be rapidly and easily inserted through a small incision using the Seldinger technique. However, each invention concept could be used individually or in any combination, both to improve known portacatheter designs and to improve methods to implant the devices.

Structural Invention Summary

Existing ports require large incisions relative to the drum diameter or are inherently unstable without suturing. Prior solutions have liabilities of design complexity and associated increased cost of manufacture, as well as requiring a large incision at the time of removal. The Structural Invention solves all these problems by permitting a port that is stable without suturing, that is simple in design, and that would not require a large incision at the time of removal.

Known ports are optimized primarily for stability and palpability through the skin at the time of Huber needle access. In the invention, the ports can be optimized for fully utilizing the skin incision, while maintaining and potentially increasing stability and palpability.

Embodiments of the Structural Invention port comprise at least three novel types of structural components: (1) lateral extensions, (2) base extensions, and (3) non-base wing extensions, all of which are designed to resist port flipping around the long axis. Each structural component comprises and is characterized as an extension from the geometric core port. At the least, an embodiment may comprise one component, two components, or all three components of the Structural Invention. Additionally, embodiments may comprise multiple sub-components, e.g., multiple and differently shaped wings or lateral extensions, if each sub-component follows the guidelines provided herein.

With respect to the lateral extension component, these are structures that extend laterally from the right and left of the core port. Embodiments of the port of the invention should meet at least one guideline condition: the side width of a port comprising lateral extensions is greater than both the base width and the top width by at least 2 mm. Within this guideline, the port lateral extensions may assume any shape. This component may be referred to as the "lateral extension component" of the Structural Invention. Examples of the lateral extension component of the Structural Invention are shown, for example, in FIGS. 1, 17, 18, 34, and 35.

In an embodiment, the widest portion of the port is at or near the equator of the incision circle; that is, near midway between the top and the base of the port device; and the side width near the equatorial level is approximately equal to or slightly greater (2-3 mm) than the diameter of the incision circle.

Figure 12A:
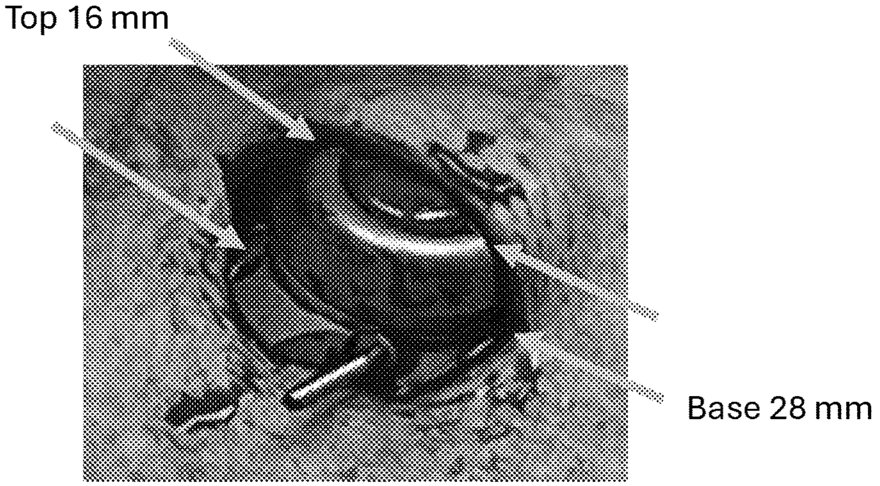
FIG. 12A, FIG. 12B, and FIG. 12C provide examples of core ports partially inserted into incisions.
Figure 12B:
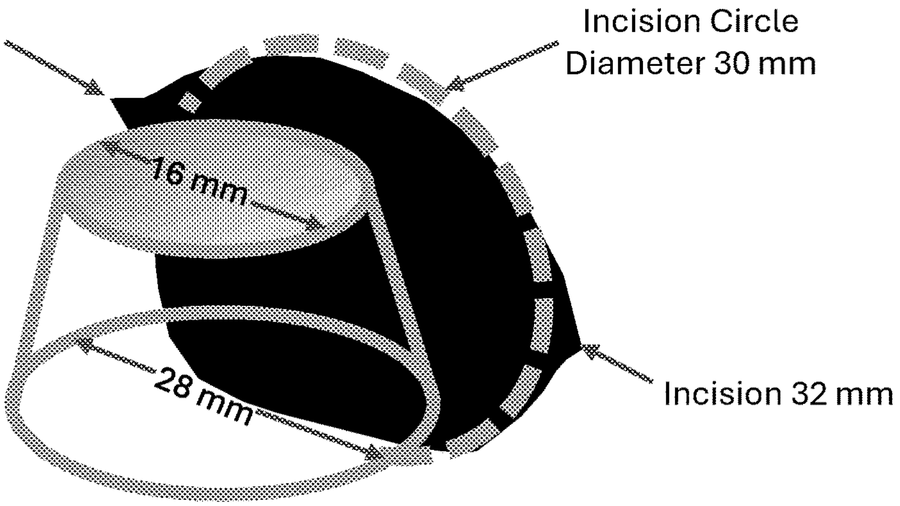
Figure 12C:
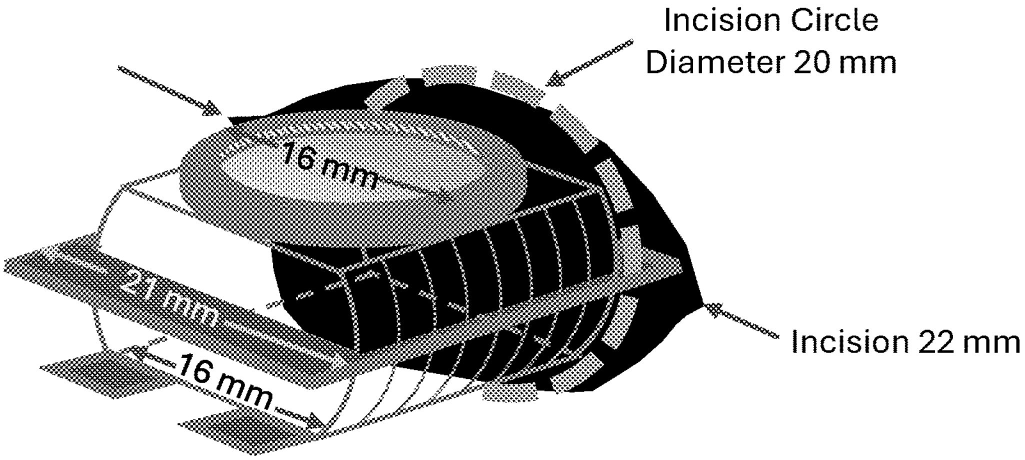

FIG. 12 provides a frame of reference for the size of port structures. The port depicted in FIG. 12A is a standard size AngioDynamics SmartPort CT (AD Catalog #H787CT80STPD0). Using the definitions herein, the top diameter is approximately 16 mm, the base diameter is approximately 28 mm, and the height is approximately 12 mm. FIG. 12B is an outline of the port of 12A, along with a cartoon of the 32 mm incision required to deliver the port through the skin. FIG. 12C illustrates an inventive port embodiment comprising a lateral extension, wherein the top is 16 mm, but the base width is narrowed from 28 to 16 mm. The overall width at the equator of the depicted embodiment port is approximately 21 mm, and the incision necessary to deliver a port of this embodiment is approximately 22 mm. Notably, while the incision lengths differ substantially, the functional core of the known port in FIG. 12B and the inventive port of FIG. 12C are identical, as is demonstrated in FIG. 13.

For further size reference, portacatheters comprise a range of sizes, including small, or "low-profile," ports. If the outline of FIG. 12B were based on a typical low-profile port, such as the Bard M.R.I. Ultra SLIMPORT depicted in FIG. 34, then the port top diameter would be approximately 12 mm, the base diameter approximately 17 mm, and the height approximately 9 mm. Insertion of the port requires an incision of approximately 19.5 mm. In FIG. 34B, lateral extensions are depicted, resulting in a port that would pass through the same 19.5 mm port incision but which would be more stable. In FIG. 34C, the base has been narrowed to 12 mm, but the lateral extensions are added for stability. The width at the equator of the depicted embodiment port is 15 mm, and the incision necessary to deliver a port of this embodiment is approximately 16 mm.

Generally, drums of known portacatheters range from 7 to 13 mm in diameter, with corresponding tops ranging from 11 to 17 mm. Port bases range from just under 17 mm to over 30 mm in diameter. Port heights range from 9 to 14 mm. In embodiments, inventive ports may be created using any combination of these dimensions.

The lateral extension component guidelines are stated with the assumption that the right and left sides of the port are symmetric mirror images. However, if the port is asymmetric, then the guideline condition is that the side lateral extent of a port comprising the lateral extension is greater than both the base lateral extent and the top lateral extent by at least 2 mm. Stated in other terms, the long axis silhouette of the inventive port is such that at least 1 side extends laterally beyond the base and top by at least 2 mm.

Figure 20A:
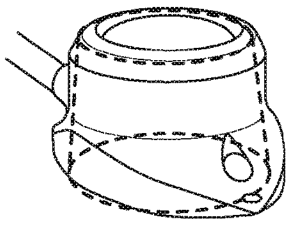
FIG. 20A, FIG. 20B, FIG. 20C, FIG. 20D, and FIG. 20E depict core ports.
Figure 20B:
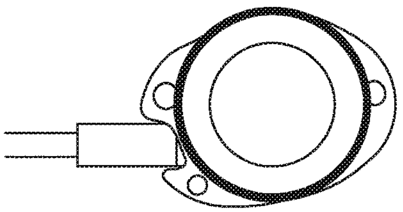
Figure 20C:
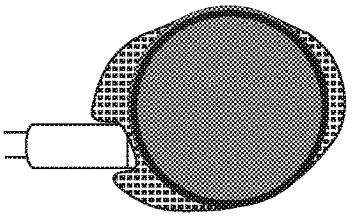
Figure 20D:
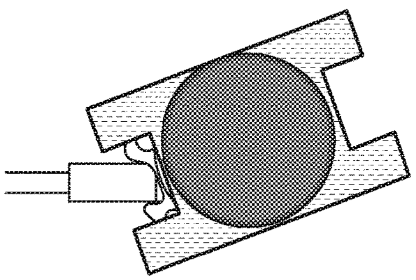
Figure 20E:
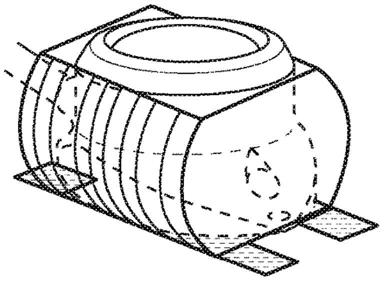

With respect to the base extension component, embodiments of the port of the invention should meet at least 3 guideline conditions: (1) the base fits within the incision circle of the core port; (2) the base plane rectangle extends by at least 2 mm both in front of and behind the base plane square; and (3) the base of the invention includes surfaces that extend to the corners of the base plane rectangle. FIG. 20D demonstrates an embodiment of a base of the invention. Other embodiments of the base are demonstrated in FIGS. 21 and 22.

The base extensions can vary in shape and configuration, so long as the base comprises a flat surface at all 4 corners of the base plane rectangle. Within this guideline, there may be a curved portion in front of or behind the base plane rectangle, as for example in FIGS. 21C and 22C. Further, the central portion of the base, in the mid-sagittal plane, may be absent, creating the appearance of front and back prongs at the base corners, as for example in FIGS. 21A and 22A.

Generally, the base extensions can vary in shape and configuration, being rectangle or curved shapes and in any combination thereof. The height of the base extensions can vary between extensions. The heights of the port base extensions are at least about 1 mm, about 2 mm, about 3 mm, about 4 mm, or about 5 mm, or having a height range from about 1 mm to about 5 mm. The base extensions can have pre-drilled holes for the ease of suturing. The base extensions may be contiguous with lateral extensions, the wing extensions, or any combination thereof.

With respect to the wing component, embodiments comprise structures comprising at least one roughly planar surface, either at the top of the wing or at the bottom. The wing originates from a level above the base and extends in front of, behind, or both in front of and behind the core port in any combination. Wings may be singular or multiple, and, if multiple, may form 90-degree or other angles with each other. Wings are designed to engage the surrounding soft tissues in a fashion like the embodiments of the base component extensions.

A wing has at least one conditional guideline, which is that a port with the wing extension structure(s) added fits within the incision circle of the core port. FIGS. 1 and 19, for example, demonstrate various wings as non-limiting embodiments of the invention.

Wings may be fixed or expanding. If expanding, wings may be mechanically expanded or self-expanding.

Dilator Invention Summary

Known ports require the performance of blunt dissection, which can be time-consuming and requires surgical skill. The Dilator Invention replaces blunt dissection with the use of either dilators, balloons, or a combination of dilators and balloons. This approach is faster, easier, and it yields a more uniformly favorable pocket.

Embodiments of the Dilator Invention consist of a dilator or set of dilators with or without balloons, as well as methods to create a pocket for a port without the need for blunt dissection. The dilator may have a non-uniform shaft, both in shape and size, as is shown in FIGS. 24, 25, 26, and 27 and described herein. The dilator may also comprise a sharpish leading edge, as is shown in FIGS. 2, 25, and 27.

Seldinger Port Invention Summary

Known portacatheters are complicated, time-consuming to implant, and difficult to exchange in or out for an existing access catheter, such as a hemodialysis catheter. The Seldinger Port Invention facilitates insertion and permits port exchanges.

The invention consists of a closeable aperture at the back of a port in alignment with the major axis of the catheter, such that a guidewire may pass freely through the port and the catheter when the port and catheter are attached. The back-end aperture may be valved to separate the reservoir from the surrounding tissues after wire removal. As an alternative, there may be a screw-in device, a snap-on device, or some other mechanism to seal the aperture after wire removal. In embodiments, the screw-in, snap-on, or other sealing device may comprise a wing or other structure to further stabilize the port. Examples of a Seldinger port are shown in FIG. 3 and in FIG. 35A.

An embodiment of the invention is that a system of devices is assembled to form a kit. The kit may include any of the devices and embodiments disclosed. For example, the kit may include a single dilator or multiple dilators, guidewire, portacatheter, catheter tubing, trocars, and so on.

DETAILED DESCRIPTION OF THE DRAWINGS

FIG. 1 is an embodiment of the Structural Invention portacatheter. Unlike known portacatheters, in this embodiment, the inventive port sides are wider than the base, the base comprises novel extensions in front of and behind the port, and there are non-base stabilizing wing extensions in front of and behind the port. The inventive port embodiment facilitates insertion by comprising a cross-section that more closely approximates the incision shape. The wider sides, novel base and wings individually and in combination resist rotation around the long axis (i.e., flipping).

FIG. 2 is an embodiment of the Dilator Invention with a transitional segment having a sharpish leading edge(s). The view is of the top aspect. In this embodiment, the front segment of the dilator (D1) is narrow, corresponding to a diameter the same size as or slightly larger than the catheter component of the portacatheter. The back segment is wider, with a diameter (D2) roughly the size of the port. The Dilator Invention replaces blunt dissection during portacatheter implantation, which speeds implantation and makes the subcutaneous pocket more favorably uniform across operators. That is, through use of the Dilator Invention, all pockets are large enough to accommodate the port without skin tension but small enough that the surrounding soft tissues constrain movement.

Figure 3A:
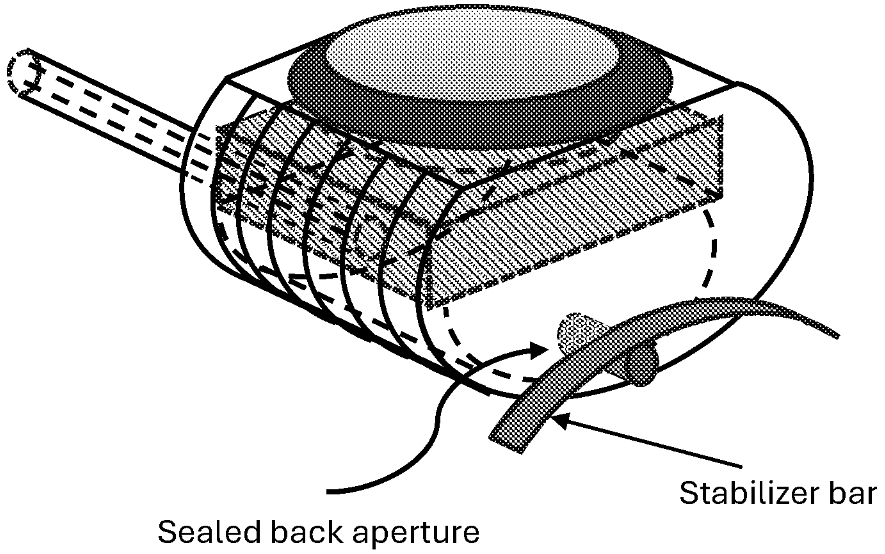
FIG. 3A and FIG. 3B depict an embodiment of a Seldinger Portacatheter having a port lumen for a guidewire in communication with the catheter lumen, comprising a combined lumen extending the entirety of the device.
Figure 3B:
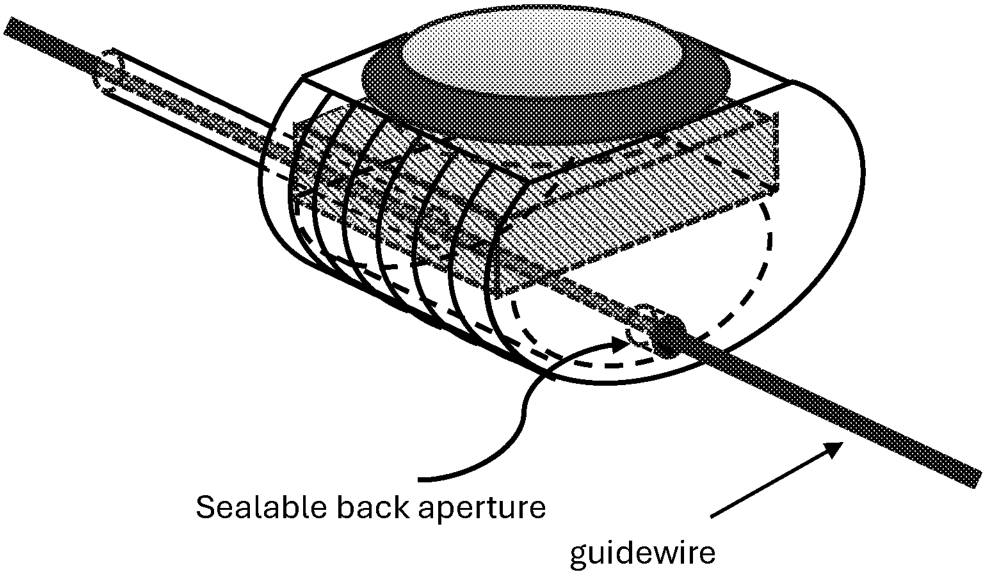

FIG. 3 is an embodiment of a Seldinger Portacatheter using a small incision. FIG. 3A demonstrates a sealable back aperture, wire removed, aperture plugged, and stabilizer bar attached to plug. FIG. 3B demonstrates a guidewire through the open sealable aperture. Expanded use of the Seldinger Technique speeds implantation and facilitates portacatheter exchanges.

FIG. 4 provides examples of collinear port and catheter long axes. FIG. 4A is an example of colinear port long axis and catheter long axis. FIG. 4B is an example of a non-collinear port and catheter long axes having angle theta.

FIG. 5 is a diagram of a core port with the base plane square and a base plane rectangle FIG. 5 demonstrates an embodiment of a core port with associated base plane square (checkerboard fill) and a base plane rectangle (dot fill). In this embodiment, the port base meets at least the following guidelines: (1) the port rectangle extends beyond the port square in front of and behind the port, and (2) the base comprises planar surfaces at the corners of the base rectangle.

FIG. 6 provides examples of geometric core ports. In FIG. 6A, the geometric core port base is wider than top. This is the basic core port shape of known portacatheters, since ports comprise bases that are wider than the top. FIG. 6B demonstrates a geometric core port base that is the same size as the top. In this case, the geometric core port coincides with the functional core port. FIG. 6C demonstrates a geometric core port, with a base narrower than top. FIG. 6D demonstrates a geometric core port with no flat base. The shape of the geometric core port in FIG. 6D is an inverted cone. The dotted line is the superimposed drawing of FIG. 6A to provide perspective.

FIG. 7 provides examples of core ports positioned over corresponding embodiments. FIG. 7 illustrates the same geometric core ports of FIG. 6 but, for each core port, the illustration below the port is an embodiment of the lateral extension component of the Structural Invention concept.

FIG. 8 provides examples of tops and a top extension of known ports. FIG. 8 shows the tops of two commercial ports, a Bard PowerPort Implantable Port (BD Catalog #SKU: 1759601, GTIN: 00801741026867) at FIGS. 8A and 8B and a Vygon Polysite 2000 at FIG. 8C, illustrating the core port top specification. In FIG. 8A, the top as defined in this document is outlined (black dotted line circle). The circle is centered over the drum and touches at least 1 side of the top triangular shape. In FIG. 8B, the triangular top is outlined (black dotted line circle), and the shaded portions (inside the rounded triangular dash-dot line) of the top outside the core port comprise known top extensions. The top extension of FIG. 8B does not meet the guidelines of inventive port extensions. In FIG. 8C, a circle again (black dotted line circle) identifies the core top. In this case, the core port top is comprised of the central drum and a circular ring around the drum. In this case, there is no top extension.

FIG. 9 provides examples of known bases, ports, and base extensions. FIG. 9A is a Vygon Polysite 2000. FIG. 9D is a Bard PowerPort Implantable Port. The solid circle line in FIG. 9B and FIG. 9D represents an outline of the core port base projected over the top (black filled-in circle) of the port. In FIGS. 9C and 9F, the base extensions of these ports are shaded (shaded area with crossed lines). These port base extensions do not meet the guidelines of inventive port extensions, as demonstrated in FIGS. 9C and 9F by a base plane rectangle overlay. Specifically, the base extensions do not include the corners of the base plane rectangle.

Figure 10A:
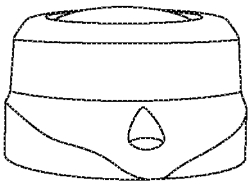
FIG. 10A, FIG. 10B, FIG. 10C, FIG. 10D, FIG. 10E, and FIG. 10F provide illustrations of the AngioDynamics Smart Port CT Mini, from different views (lateral view.
Figure 10B:
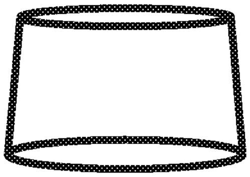
Figure 10C:
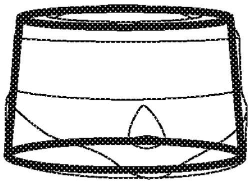
Figure 10D:
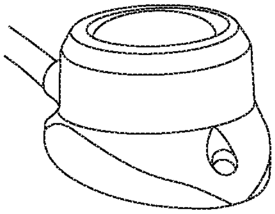
Figure 10E:
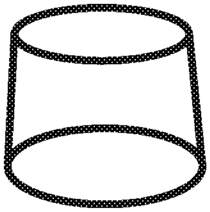
Figure 10F:
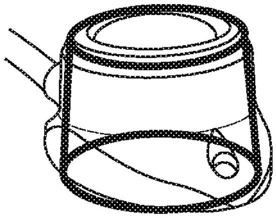

FIG. 10 is an illustration of a core port of the AngioDynamics Smart Port CT Mini portacatheter, wherein the black outline comprises the core port, and the checkered portions of FIG. 10C comprise known lateral extensions. Notably, the lateral extensions do not result in a side width greater than the base or top width, and therefore the lateral extensions do not meet the guidelines of an inventive port.

Figure 11A:
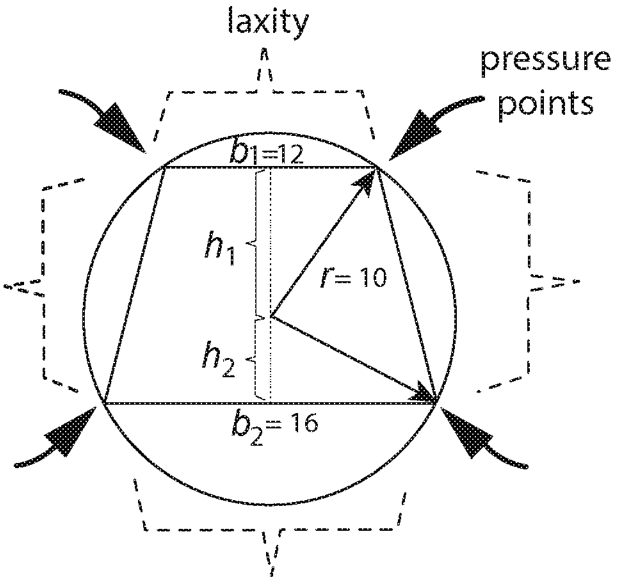
FIG. 11A and FIG. 11B represent the incision circle concept.
Figure 11B:
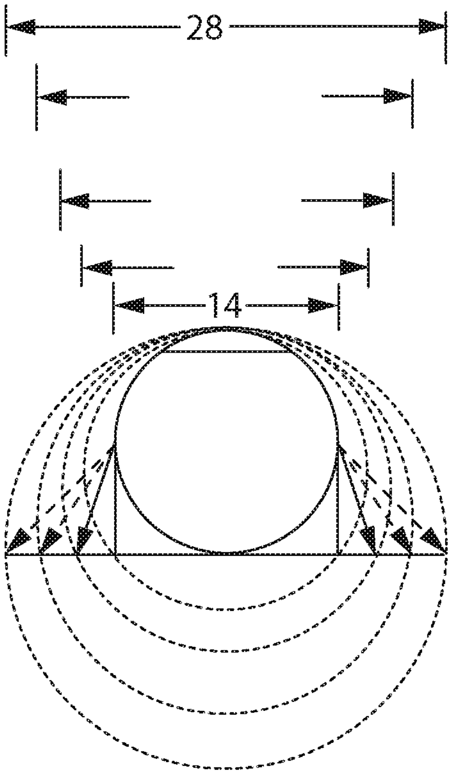

FIG. 11 represents the incision circle concept. The long-axis cross-sections of a core port are symmetric trapezoids, with the largest trapezoid at the cross-section bisecting the top and base. FIG. 11A demonstrates the incision circle of the core port, which intersects the angles of the trapezoid, see curved arrows, and identifies contact points with increased pressure. Also illustrated is that the greatest restriction to insertion occurs at the angles of the trapezoid, with regions of laxity primarily at the sides as shown with the dotted line braces. FIG. 11B demonstrates that, as the base of a port widens, the incision circle necessary to accommodate the port becomes larger. The specific values in mm of FIG. 11B are for purposes of illustration and are not limiting.

FIG. 12 provides examples of core ports partially inserted in incisions. FIG. 12A is a photograph of a partially inserted AngioDynamics port having a top width of 16 mm and bottom base width of 28 mm. The incision size is about 32 mm. FIG. 12B is a representation of a known port insertion in the approximated incision shape taken from the photograph in FIG. 12A. FIG. 12C is a representation of an embodiment port insertion. The ports of FIGS. 12B and 12C have identical top circles, but the port of FIG. 12B has a broad base, with a correspondingly large incision and incision circle. Contrariwise, the embodiment port of FIG. 12C has a narrow base (16 mm) with widened sides (21 mm), and the corresponding incision (22 mm) and incision circle (20 mm) are smaller. Incision length and incision circle values are approximations for purposes of illustration and are not limiting.

Figure 13A:
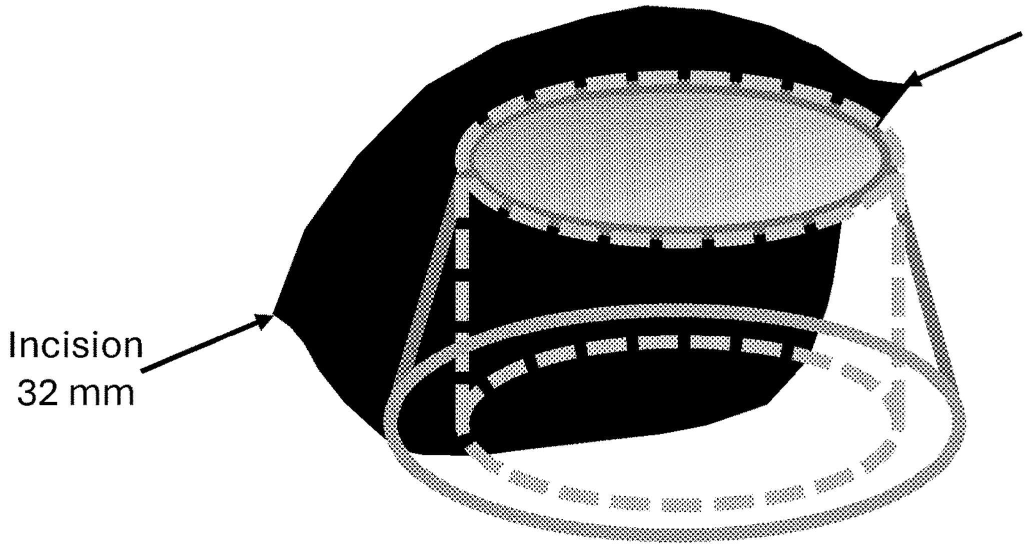
FIG. 13A and FIG. 13B demonstrate ports entering representative incisions.
Figure 13B:
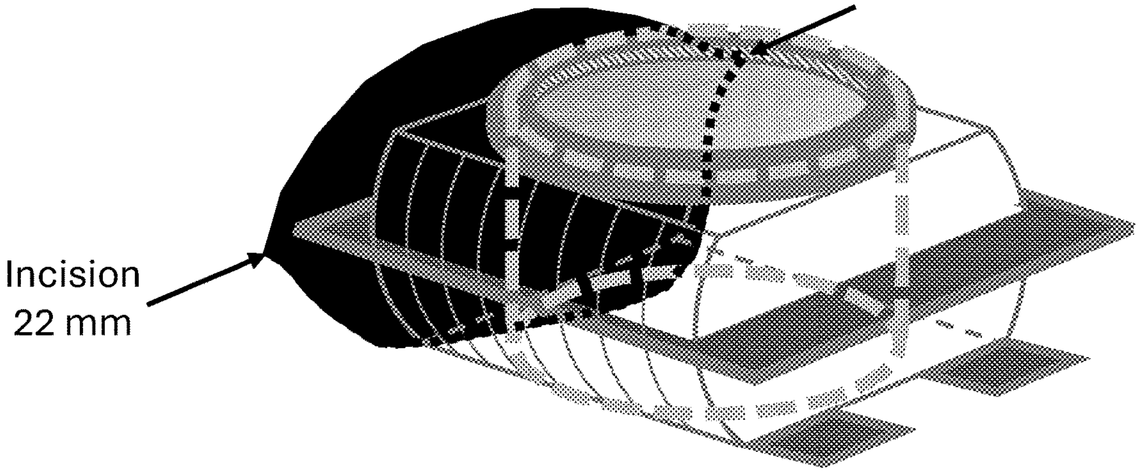

FIG. 13 provides examples of a known broad base port vs an embodiment having the same functional core, but a smaller base and a smaller incision. FIG. 13A demonstrates a functional core port (dashed line cylinder) within a known geometric core port (solid line). FIG. 13B demonstrates the identical functional core port (dashed line), but within an embodiment of a port (solid line) of the invention. Since the widths of the top and base of the port in FIG. 13B are the same as the known port, the geometric core port and the functional core port coincide. Because the port of FIG. 13B (1) has a narrower base than the device in 13A, and (2) the port follows the guidelines of the invention, the corresponding incision for the port in FIG. 13B is smaller. Incision length values are approximations for purposes of illustration and are not limiting.

FIG. 14 provides examples of incision circles and incisions to illustrate a stable port through a smaller incision. FIG. 14 demonstrates a comparison of the size of the incision circles and incisions necessary to implant a typical known port, with a trapezoidal cross-section, compared to an embodiment of the invention. FIG. 14A demonstrates a known port cross-section trapezoid within an incision (solid line) and within an incision circle (dotted line). In an embodiment, FIG. 14B demonstrates a port within an incision (solid line) and within an incision circle (dashed and dotted line). While the top widths of the ports and the heights of the ports in FIGS. 14A and 14B are of identical size—that is, the functional cores are identical—the incision and incision circle of the inventive port are smaller. The incision circles and the incisions are overlayed in FIG. 14B and FIG. 14C, respectively, to demonstrate the differences in size. FIG. 14E demonstrates that the known port, with the identical top and height as the inventive port, would not fit through the smaller incision circle nor within the smaller incision of the inventive port.

Figure 15A:
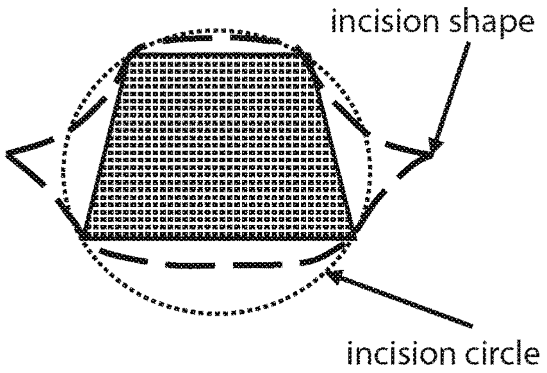
FIG. 15A and FIG. 15B depict port cross-sections set in their corresponding incision shape and incision circle.
Figure 15B:
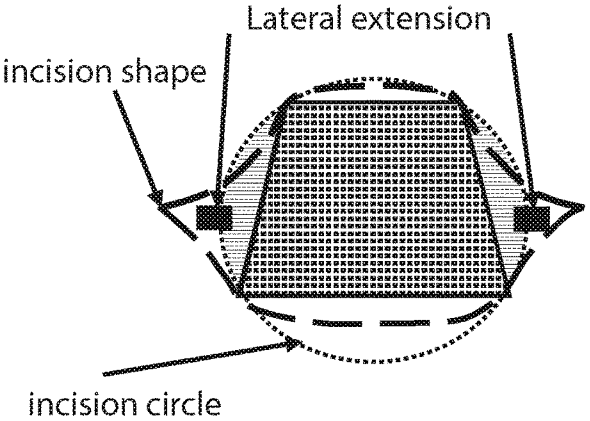

FIG. 15 is an example of the relationship between an incision circle and an incision for a more stable inventive port passing through the same incision as a less stable known port. FIG. 15A demonstrates a typical known port cross-section with corresponding incision shape (long dash line) and incision circle (dotted line). FIG. 15B demonstrates an inventive embodiment with the same core port but with inventive lateral extensions (black rectangles and rounded darker shading) of the Structural Invention. The port of FIG. 15B would be more stable in the pocket, due to additional friction associated with widened sides and further restriction based on the additional planar extension engaging the surrounding soft tissues.

Figure 16A:
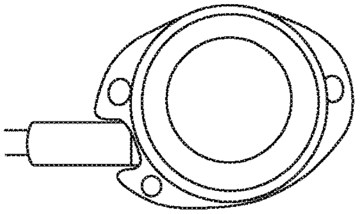
FIG. 16A, FIG. 16B, FIG. 16C depict a port.
Figure 16B:
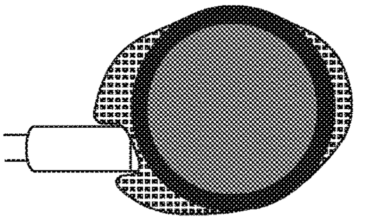
Figure 16C:
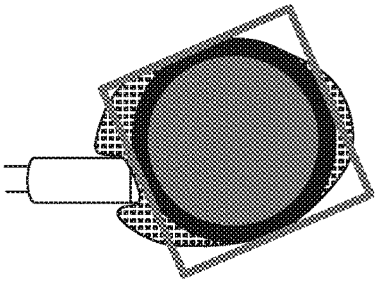

FIG. 16 is an example of a known portacatheter base extension, demonstrating why the extension does not meet the guidelines. FIG. 16A is an AngioDynamics Smart Port CT Mini as viewed from the top. In FIG. 16B, the base extensions of the port in FIG. 16A are highlighted (checkerboard). In FIG. 16C, a base square and, in this case, rectangle is outlined (gray rectangle) and superimposed onto the image. The base does not extend to the corners of the base rectangle.

Figure 17A:
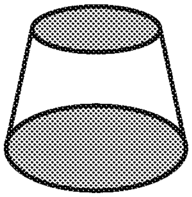
FIG. 17A, FIG. 17B, and FIG. 17C depict a core port.
Figure 17B:
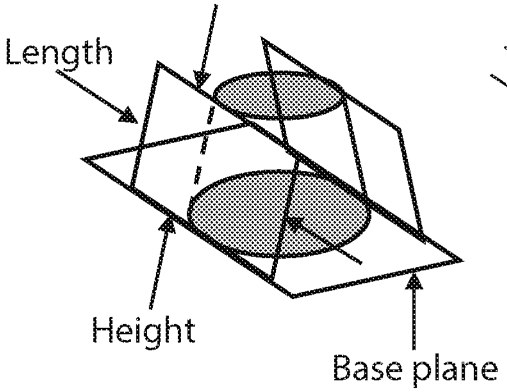
Figure 17C:
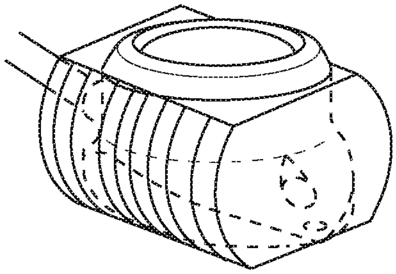

FIG. 17 provides diagrams of a core port, a core port plus sidewall rectangles, and a corresponding port embodiment of the invention. FIG. 17 is an embodiment of the lateral extension component of the Structural Invention which exemplifies the lateral sidewall concept. In this embodiment, the lateral sidewall extension results in a roughly circular port embodiment. FIG. 17A demonstrates a core port as an upright truncated cone. FIG. 17B demonstrates the potential orientation of the sidewall rectangles and dimension labels for the length of the sidewall rectangle and the height of the sidewall rectangle are shown. The base plane is also shown. FIG. 17C demonstrates an embodiment of the invention illustrating the lateral sidewalls extending beyond the width of the base but extending to the base plane in both directions of the width and length of the base plane.

Figure 18A:
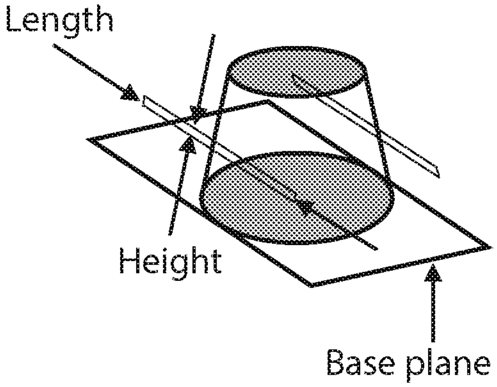
FIG. 18A and FIG. 18B depict a core port.
Figure 18B:
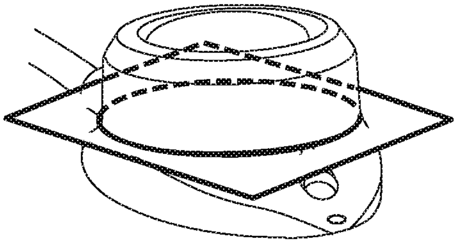

FIG. 18 provides diagrams of a core port, a core port base rectangle, and core port sidewall rectangles. FIG. 18 illustrates an embodiment of the lateral extension component of the Structural Invention concept, again exemplifying the lateral sidewall concept. In FIG. 18A, there are rectangular-based sidewalls, but the height of the lateral sidewall rectangle is minimal. The sidewall rectangles and dimension labels for the length of the sidewall rectangles and the height of the sidewall rectangle are shown. The lateral sidewall extension in this case is roughly planar, as depicted in FIG. 18B. In FIG. 18B, the lateral sidewalls extend beyond the width of the base but do not extend to the base plane. In this example, the front and back port sides also demonstrate planar wings of the invention that are continuous with the lateral sidewalls, making the stabilizing shape a plane surrounding the core port centered at or near the incision circle equator. The sidewalls and wings may or may not extend beyond the base plane.

FIG. 19 provides embodiments of port wings extending from the front and back of a portacatheter. FIG. 19 demonstrates embodiments of wings (non-base wings) of the Structural Invention concept extending in front or behind the port (arrows).

FIG. 20 demonstrates a known base extension and an embodiment of a base extension of the invention. FIG. 20A illustrates an AngioDynamics Smart Port CT Mini with the corresponding core port overlay (dashed lines). FIG. 20B is a top view of the same port as in FIG. 20A with a drawn overlay (black circle) identifying the core port base circle. FIG. 20C illustrates the top view as in FIG. 20B but with known base extensions highlighted (checkerboard filled in space). FIG. 20D illustrates an embodiment of the base component of the Structural Invention concept illustrating the base extensions (dotted filled in space). FIG. 20E is a perspective rendering of a port embodiment that includes the same base extension as that shown in FIG. 20D (dotted filled in space).

Figure 21:
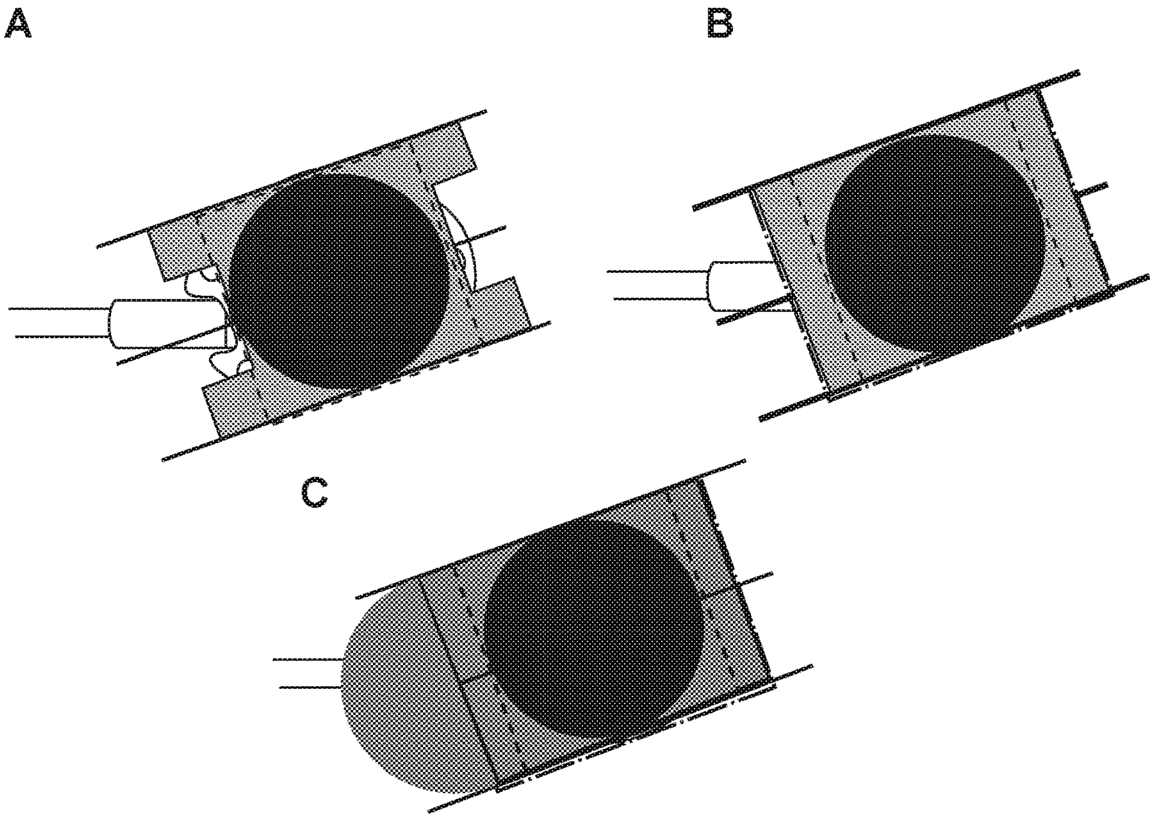
FIG. 21 demonstrates base extension embodiments of portacatheters with a variety of base configurations.

FIG. 21 demonstrates embodiments of base extensions, with a variety of base configurations that meet the guidelines for base extensions.

Figure 22:
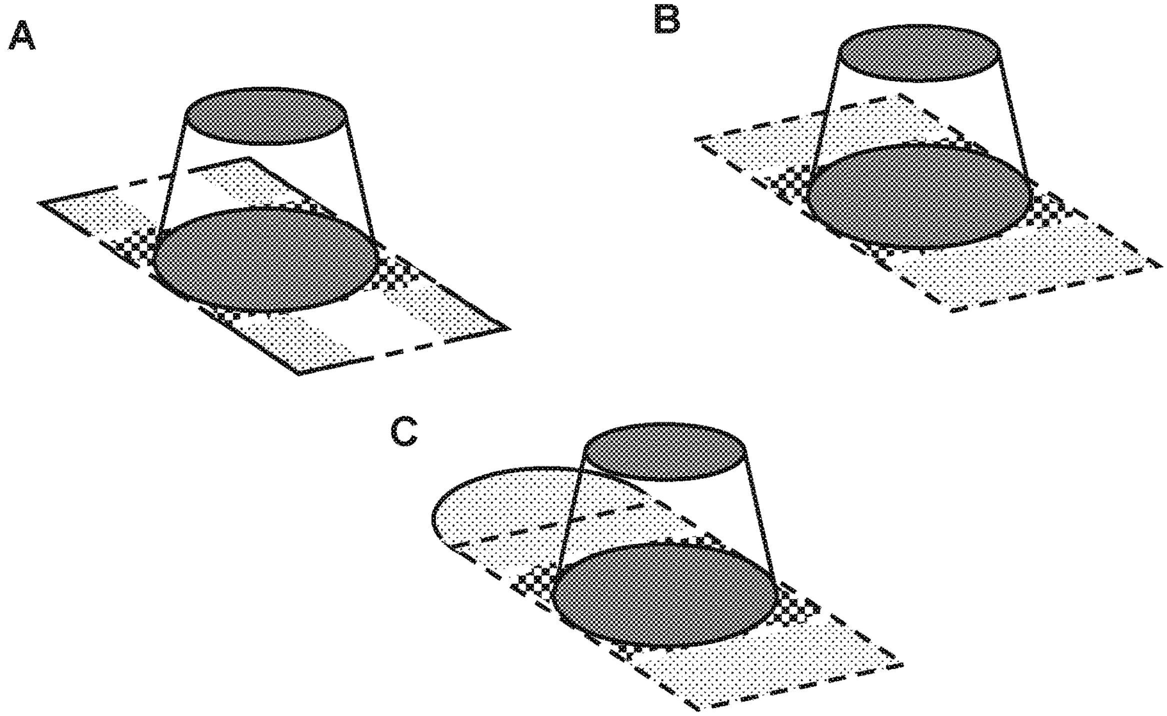
FIG. 22 demonstrates the same base extension (dotted filled space) embodiments as shown in FIG. 21 but from a different perspective.

FIG. 22 demonstrates the same base extension embodiments as are shown in FIG. 21 but from a different perspective. The base plane rectangle (outer perimeter black dotted line) is at least 2 mm beyond the base plane square (checkerboard). The base extensions (dotted filled space) extend to the corners of the base plane rectangle.

The base extensions can vary in shape and configuration, so long as the base comprises a flat surface at the corners of the base plane rectangle. Within this guideline, there may be a curved portion in front of or behind the base plane rectangle, as for example in FIGS. 21C and 22C. Further, the central portion of the base, in the mid-sagittal plane, may be absent, creating the appearance of front and back prongs at the base corners, as for example in FIGS. 21A and 22A.

FIG. 23 demonstrates known tunnelers or trocars.

Figure 24A:
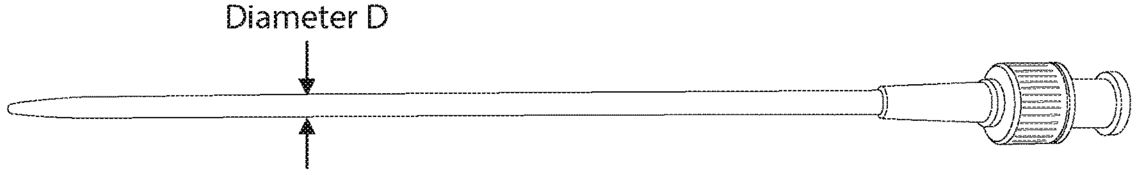
FIG. 24A and FIG. 24B depict dilators.
Figure 24B:
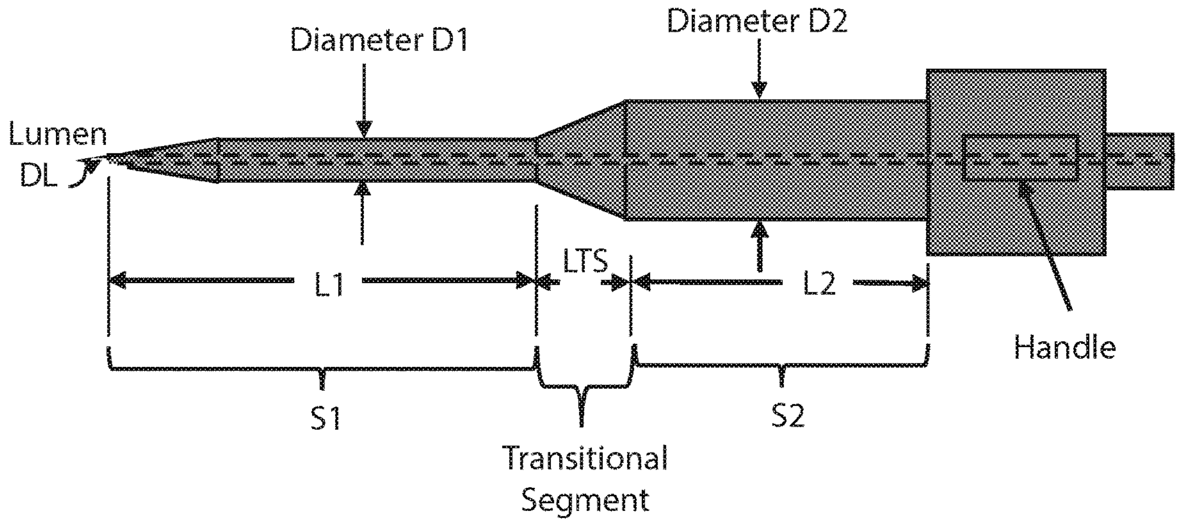

FIG. 24 demonstrates a simple dilator and an embodiment of a complex dilator. In FIG. 24A, the simple dilator comprises a tapered front, a hub at the back, and a uniform cylindrical shaft between them having diameter (D). FIG. 24B is the top aspect view of an example of a complex dilator comprising at least 3 shaft segments, a front segment (S1) with diameter D1 and length L1, a back segment (S2) with diameter D2 and length L2, and a transition segment (TS) with a length LTS between segments S1 and S2. The lumen has a diameter (DL).

Figures 25A, 25B, 25C:
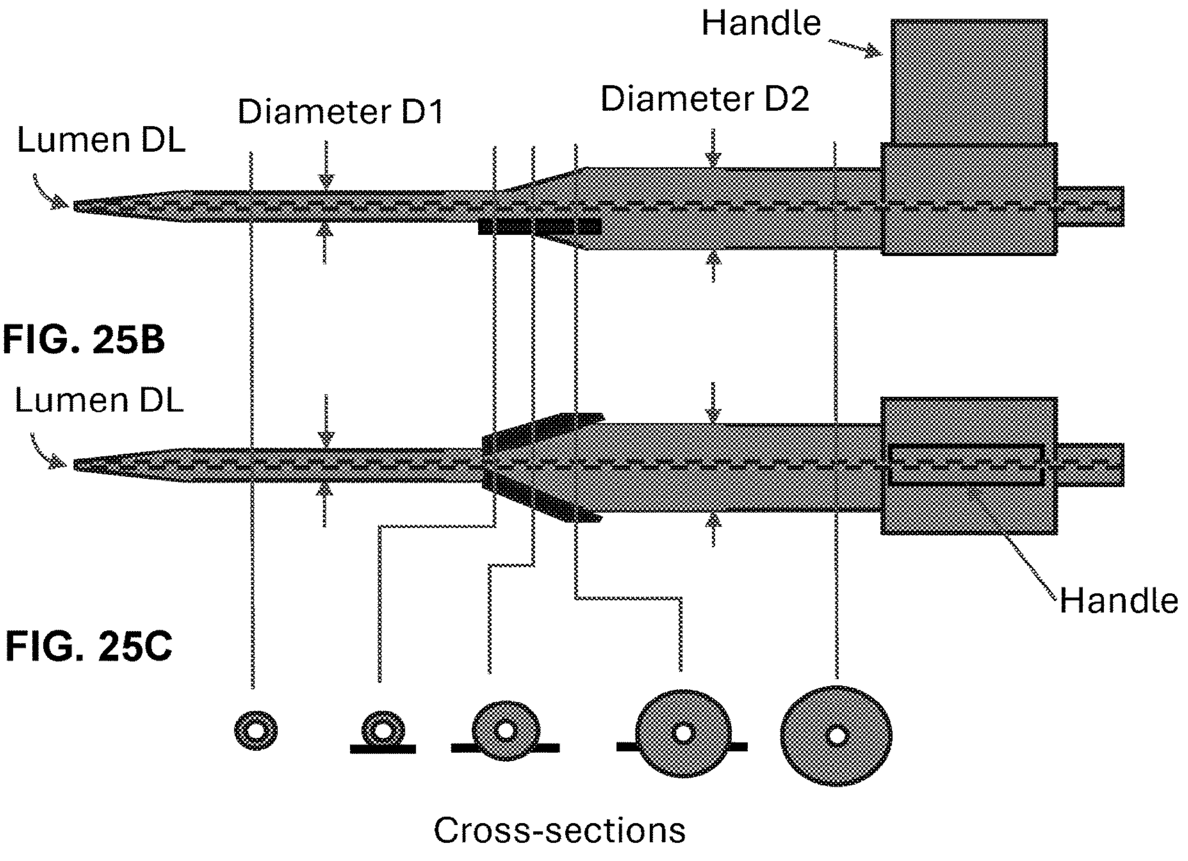
FIG. 25A, FIG. 25B, and FIG. 25C depict views of a complex dilator.

FIG. 25 is an example of a dilator with transitional segments having sharpish leading edge(s). FIG. 25A demonstrates a lateral aspect view, and FIG. 25B demonstrates a top aspect view of a dilator embodiment, wherein there is at least one sharpish leading edge at the transition segment (TS). There can be one, two, three, four, five, six, or more sharpish leading edges. FIG. 25C shows various cross-sections of the device at the provided cross-sectional cross-line through the device.

Figure 26A:
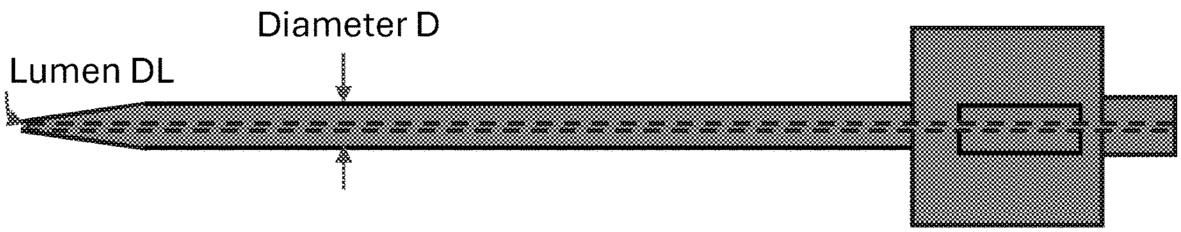
FIG. 26A, FIG. 26B, and FIG. 26C demonstrate a set of dilators.
Figure 26B:
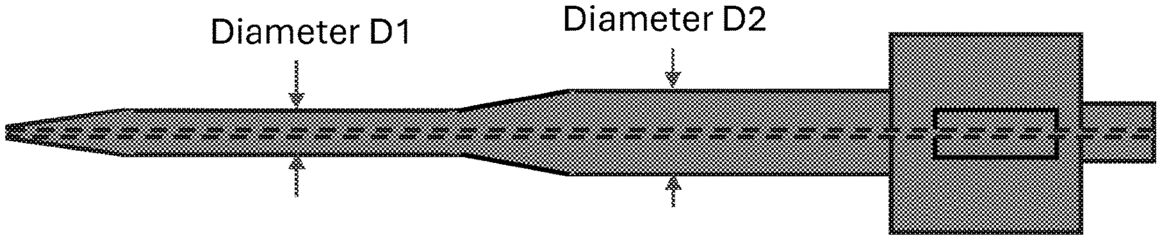
Figure 26C:
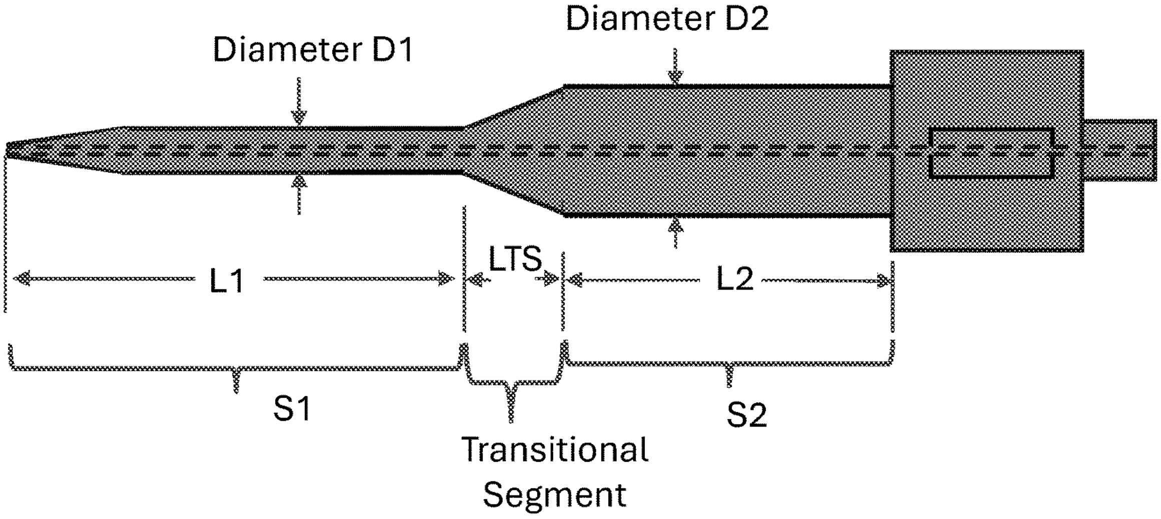

FIG. 26 is example of a dilator series embodiment. FIG. 26 demonstrates a set of dilators (potentially as part of a kit for implantation of devices), wherein the segment 2 (S2) increases in diameter. The first dilator (FIG. 26A) has a uniform shaft having diameter D, the second dilator (FIG. 26B) comprises a S1 having diameter D1 and a larger S2 segment having diameter D2, with a transition segment, TS, in bridging the S1 and S2 via a taper. The third dilator (FIG. 26C) is like the second dilator (FIG. 26B), but the S2 has a larger diameter D2 than in the device in FIG. 26B. During portacatheter implantation, the initial dilator would be used to establish a path large enough to accommodate the catheter. Subsequently, the larger S2 segments open the proximal space to make it large enough to accommodate the port. The S2 segments can be varied to accommodate the port size and port shape.

Figures 27A, 27B, 27C:
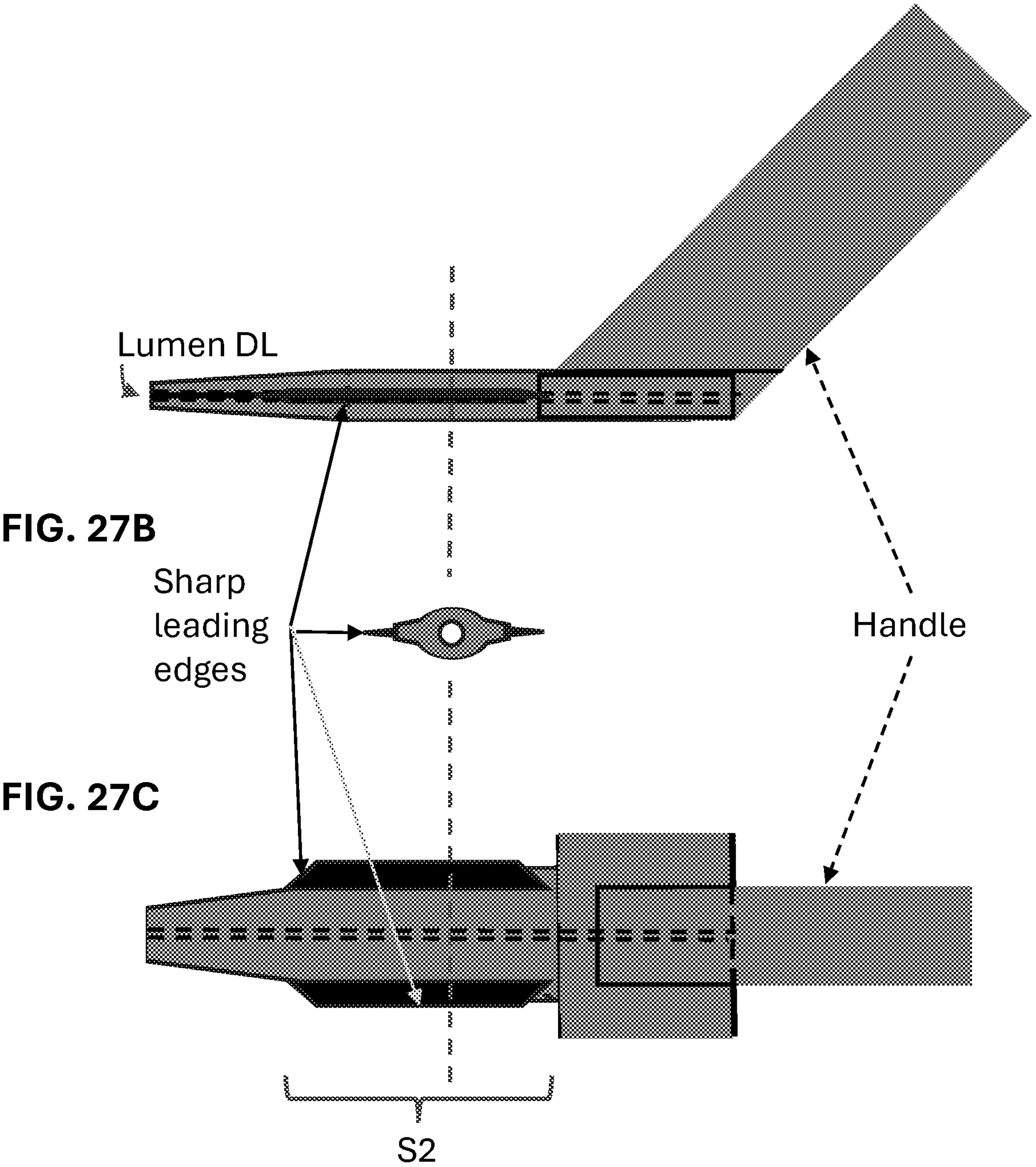
FIG. 27A, FIG. 27B, and FIG. 27C depict views of an example of a dissector dilator.

FIG. 27 is another example of a dilator, referred to herein as a dissector dilator. This represents a particular embodiment of the dilator invention, wherein the device is flatter, e.g., ovoid, and contains a transition segment leading edge. The lateral aspect is represented in FIG. 27A, the top aspect is represented in FIG. 27C, and the cross section is represented in FIG. 27B. The location of the cross-section is identified by the vertical dashed line. In each of the panels the sharpish leading edges are identified by the solid arrows. The handle is identified by the dotted line arrows. The primary purpose of this dilator would be to dissect the soft tissues over the S2 segment. This would diminish the contusion and subsequent hematoma associated with advancing the larger S2 segments and the portacatheter for pocket creation.

Figure 28A:
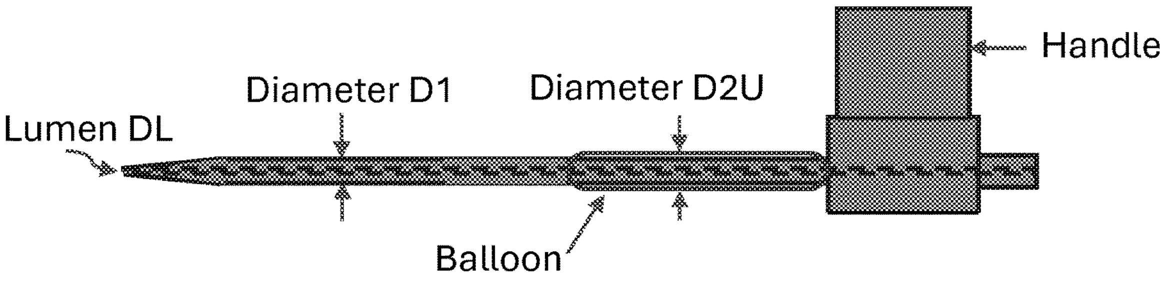
FIG. 28A and FIG. 28B depict a complex dilator invention having a balloon at the S2 segment.
Figure 28B:
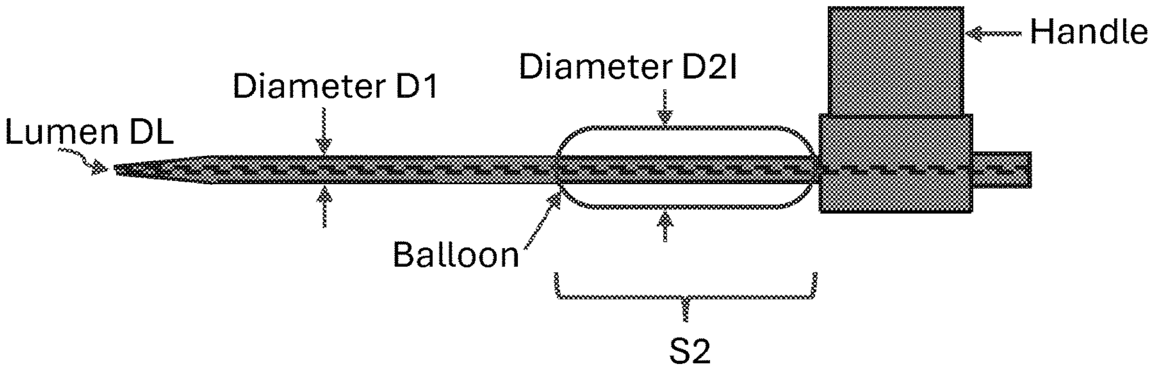

FIG. 28 is a special case example of the complex dilator invention, wherein the S2 segment comprises a balloon. In this case, after dilator insertion, the balloon is inflated to expand the S2 segment to a size and/or shape that could accommodate the port. The balloon can be circular, ovoid, or some other shape in cross-section, for example, matching the general shape of the portacatheter device. The balloon could be a "cutting balloon," where in the balloon circumference comprises thin longitudinal blades, e.g., the Boston Scientific Peripheral Cutting Balloon, product code M001PCB5020500. FIG. 28A shows the ballon uninflated having diameter D2U and FIG. 28B shows the balloon inflated having a larger diameter D2I.

Figure 29A:
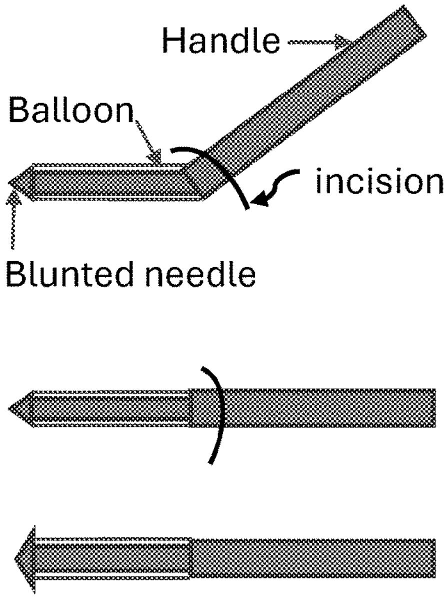
FIG. 29A and FIG. 29B provide examples of trocars having a blunted needle front end with a balloon.
Figure 29B:
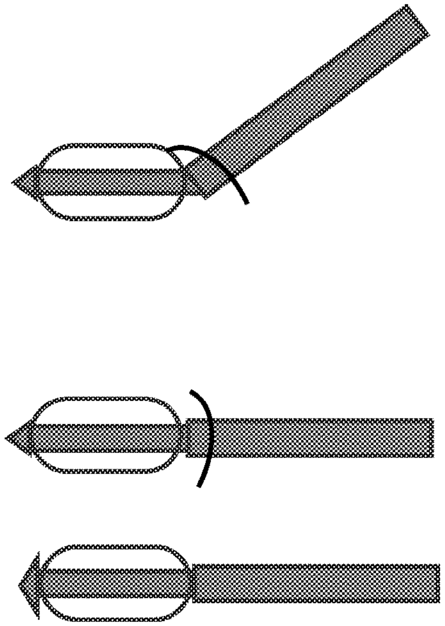

FIG. 29 represents a trocar version of the dilator invention, wherein the operator advances the trocar as one would the tunneller. However, in this case, the balloon is positioned on the trocar itself, and the pocket is created without the need for a continuous wire. This version of the invention would be useful for establishing a pocket in the setting of a port incision that is cranial to the port as it is inserted. In FIG. 29A, the illustrations demonstrate when the balloon is not inflated. The top drawing illustrates the side view the device having a blunted needle, the middle drawing illustrates the top view of the device with a narrow semi-sharp front to create a straight and narrow path, and the bottom drawing illustrates the top view with a broad semi-sharp front to create a broad path. In FIG. 29B, the top, middle, and bottom illustrations demonstrate when the balloon is inflated for each of the top, middle, and bottom depictions in FIG. 29A, respectively.

Figure 30A:
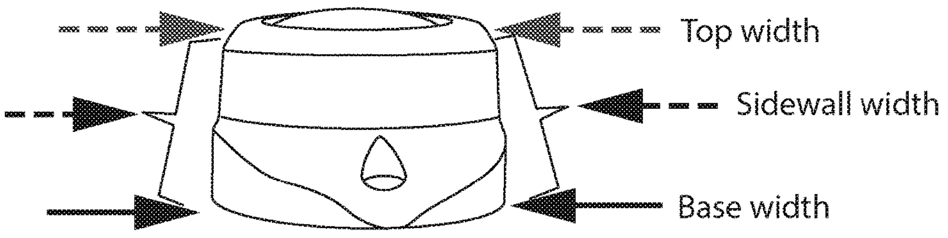
FIG. 30A, FIG. 30B, and FIG. 30C depict ports.
Figure 30B:
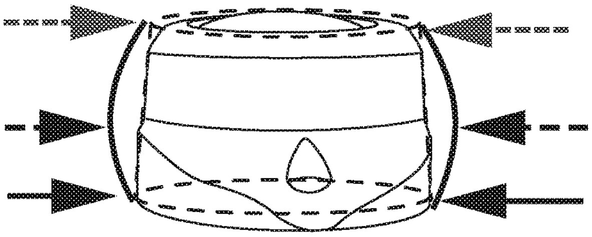
Figure 30C:
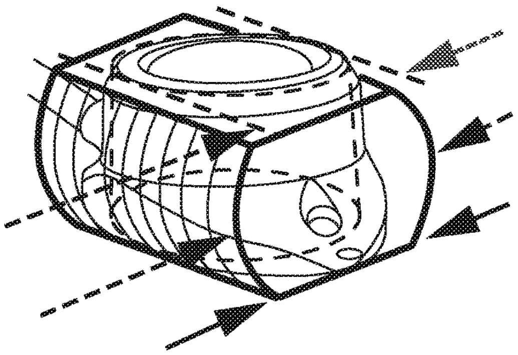

FIG. 30 demonstrates the concept of the sides-wider-than-top-and-bottom, which is part of the lateral extension component of the Structural Invention concept, with the lateral extension rounded, creating a roughly circular port cross-section. FIG. 30A illustrates a known port having a top width, a sidewall width, and a base width and wherein the base width is greater than the sidewall width. FIG. 30B is an example of a port having a sidewall width wider than the base width and wider than the top width. The port perimeter (black outline) of FIG. 30A is overlayed on the device and the outline of the sidewall extensions (black lines) are shown. FIG. 30C is the same device as depicted in FIG. 30B as viewed from a different perspective. Additional outlines of the device (black lines) are shown. Each drawing of a device identifies the top width (dotted line arrows), the sidewall width (dashed line arrows), and the base width (solid line arrows).

Figure 31A:
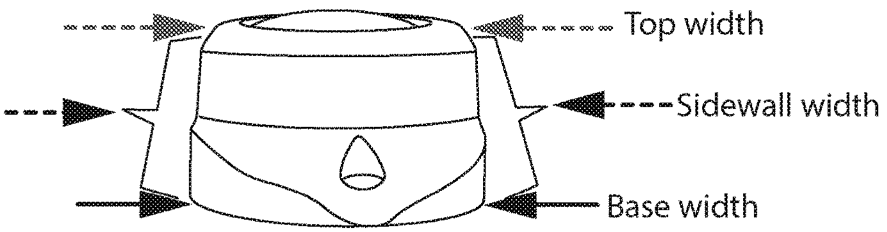
FIG. 31A, FIG. 31B and FIG. 31C depict ports.
Figure 31B:
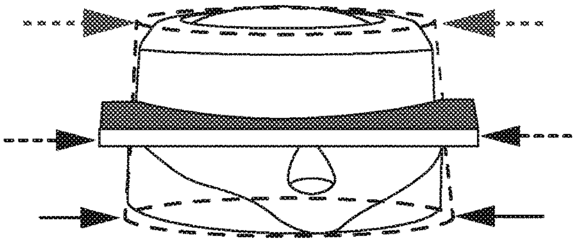
Figure 31C:
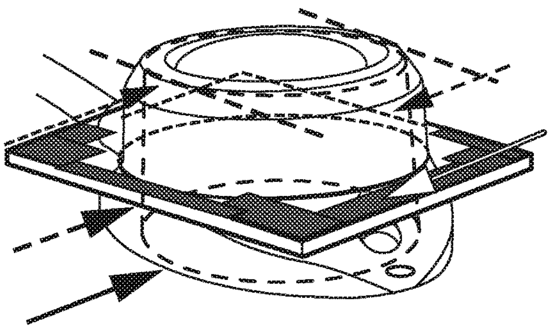

FIG. 31 is another demonstration of the concept of the sides-wider-than-top-and-bottom, except with the lateral extension roughly planar rather than rounded. FIG. 31A illustrates a known port having a top width, a sidewall width, and a base width and wherein the base width is wider than the sidewall width. FIG. 31B is an example of a port having a sidewall width wider than the base width and wider than the top width. The port perimeter (black outline) of FIG. 31A is overlayed on the device. The thickness of the planar lateral extension is determined in the height axis. In this example, the lateral extension is roughly located at the midpoint of the height axis. FIG. 31C is the same device as depicted in FIG. 31B as viewed from a different perspective. Each drawing of a device identifies the top width (dotted line arrows), the sidewall width (dashed line arrows), and the base width (solid line arrows).

FIG. 32 demonstrates various embodiments of the lateral extension component of the Structural Invention concept. The incision circle (black circle) is drawn around the devices in FIGS. 32A, 32B, and 32C. FIGS. 32A and 32D show the same device from different views. The device has lateral extensions that are rounded and the sides extend from the bottom to the top. FIGS. 32B and 32E show the same device from different views. The device comprises lateral extensions that are rounded near the base, but that flatten near the midpoint of the height axis to make a horizontal plane. FIGS. 32C and 32F show the same device from different views. The device in FIGS. 32C and 32F is identical to that of FIGS. 32B and 32E, however there are also base extensions at each of the base rectangle corners that may or may not extend beyond the lateral extensions. In FIG. 32C, the dimension arrows with dotted lines depict a potential height of the base extension as determined in the height axis.

Figure 33A:
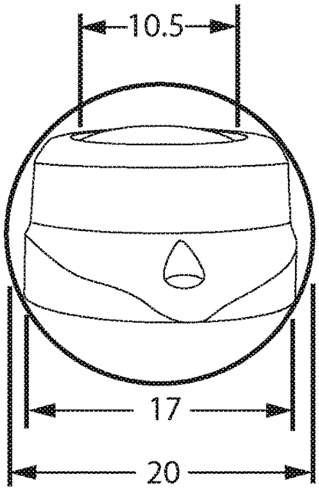
FIG. 33A, FIG. 33B, FIG. 33C depict ports.
Figure 33B:
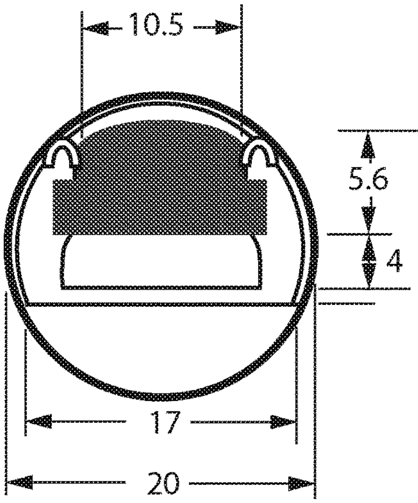
Figure 33C:
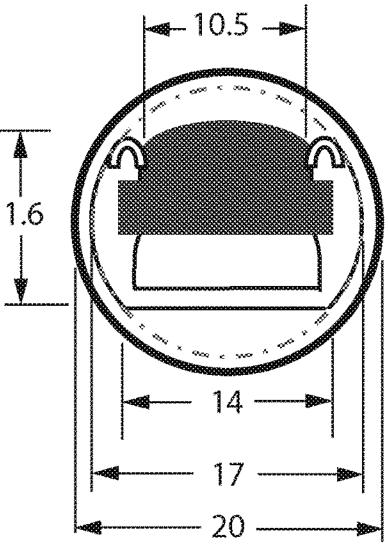

FIG. 33 demonstrates how the lateral extension component of the Structural Invention concept may be used to narrow the base in a fashion that permits a smaller incision for implantation while increasing stability. In FIG. 33A, an AngioDynamics Smart Port CT Mini is viewed from the back and has a drum diameter of about 10.5 mm, a top of about 14.5 mm, and a base width of about 17 mm. The incision size for implantation is about 22 mm. The incision circle (black circle surrounding the port) diameter is about 20 mm. FIG. 33B is a cross-section of a comparable embodiment having a similar top width and base width as the port depicted in FIG. 33A. Here, however, the lateral sides have been extended outward, so that the port width is greater at the lateral sides than at the base or top. Nevertheless, the port still fits within the same incision circle as the known port and therefore would be expected to fit within roughly the same actual incision. In FIG. 33C, the port base has been narrowed from 17 mm to 14 mm. In this example, the incision circle (circle having a dashed and dotted line) is smaller than the incision circle (circle having solid line) of the known port device depicted in FIG. 33A, so the device port depicted in FIG. 33C would fit through a smaller incision than the ports of FIG. 33A or FIG. 33B, approximately 19 mm. This smaller incision is possible even though all 3 port devices comprise the same functional core port. All dimensions are in millimeter (mm).

Figure 34A:
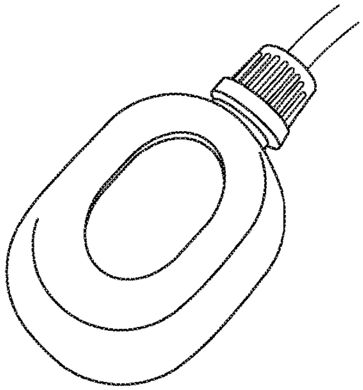
FIG. 34A, FIG. 34B, and FIG. 34C depict ports.
Figure 34B:
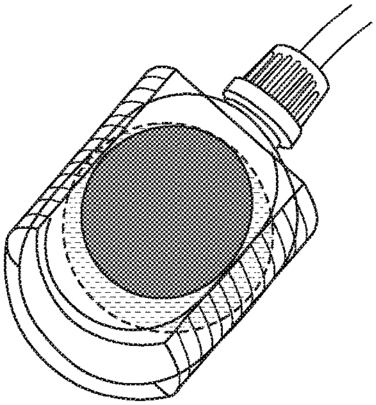
Figure 34C:
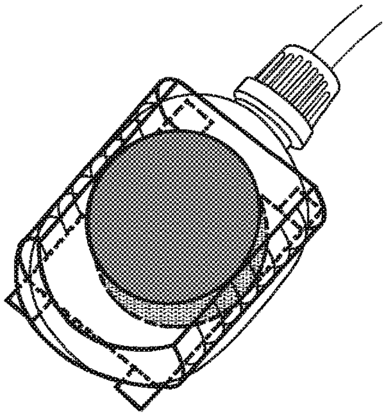

FIG. 34 demonstrates another example of how the lateral extension component of the Structural Invention concept may be used to stabilize an existing port or to narrow the base in a fashion that permits a smaller port incision. FIG. 34A shows the Bard M.R.I. Ultra SLIMPORT that utilizes a minimal incision of about 19.5 mm. FIG. 34B is a modified version of the port as depicted in FIG. 34A, but with the corresponding geometric core port, (where the base width is wider than top and is the basic core port shape of all known portacatheters) and with the addition of lateral extensions superimposed on the image of FIG. 34A. The port of FIG. 34B would be more stable in the pocket than the original port of FIG. 34A while still utilizing an incision of about 19.5 mm long. In FIG. 34C, the port base has been narrowed from the device depicted in FIG. 34B, such that the port base and top are the same size. This is illustrated by the superimposed core port, which is now cylindrical in shape (the top and bottom are of the same width). This is an example of a geometric core port and a functional core port that coincide. The port of FIG. 34C would fit through a smaller incision than the ports of FIG. 34A or FIG. 34B, about 16.5 mm.

Figure 35A:
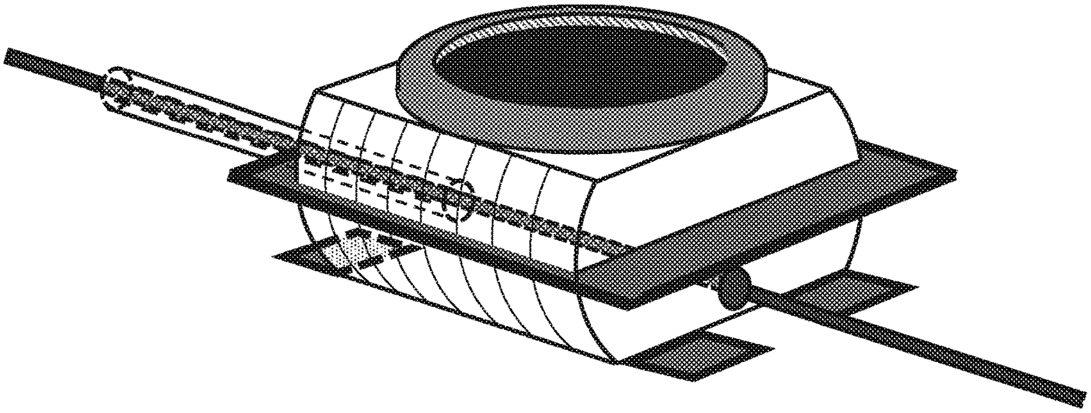
FIG. 35A and FIG. 35B depict ports.
Figure 35B:
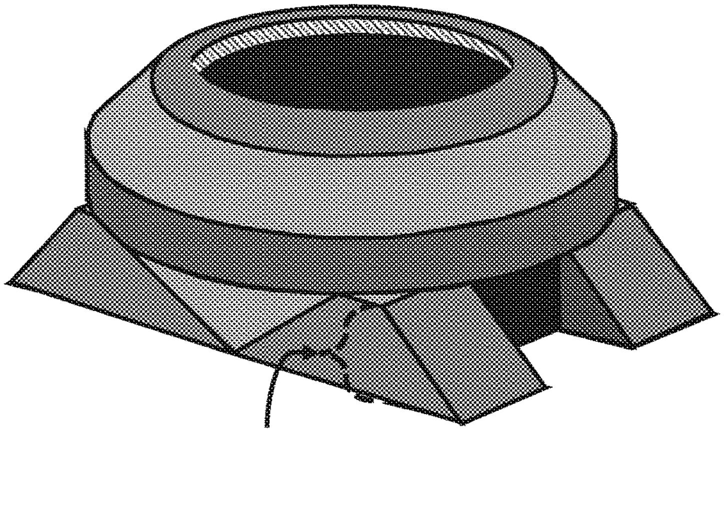

FIG. 35 depicts alternative embodiments. FIG. 35A illustrates another design that could be used for a Seldinger Portacatheter. FIG. 35B illustrates a port with a complex design, at least having base extensions that taper and having a height (curved arrow at dotted line brace) that nevertheless meets the guidelines for a port of the invention.

Figure 36A:
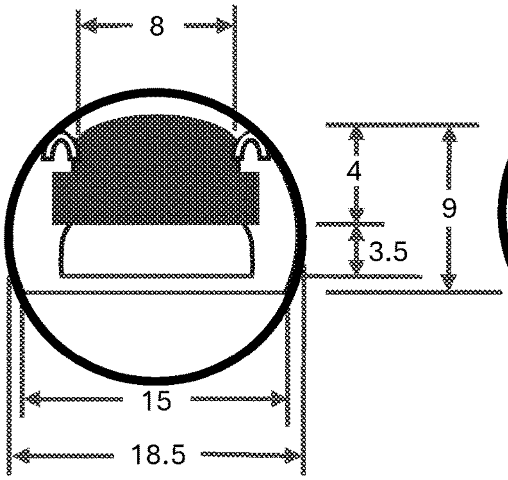
FIG. 36A, FIG. 36B, and FIG. 36C illustrate simplified cross-sections of various embodiments of portacatheter devices having variable base widths.
Figure 36B:
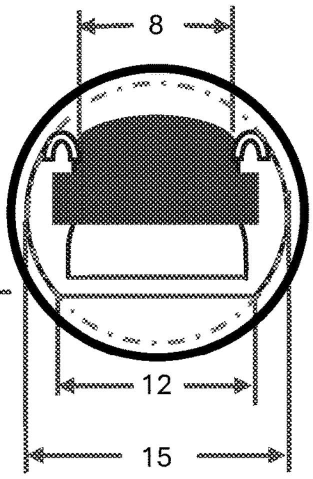
Figure 36C:
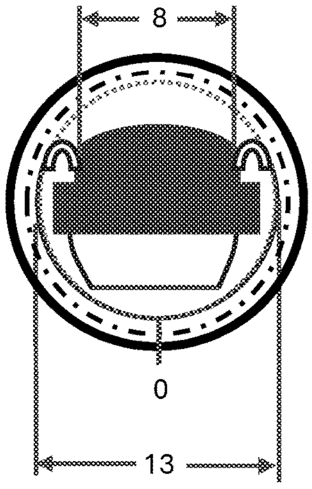

FIG. 36 provides examples of embodiments of low-profile ports with lateral extensions increasing stability and narrowing the incision for implantation. FIG. 36 demonstrates that a port with a rounded base could fit through a smaller incision than a port with a flat base. The example port in FIG. 36A, with an about 12 mm top, an about 8 mm drum, and an about 15 mm base would utilize about a 19.5 mm to about 20 mm length incision, while having an incision circle (black outer circle) of about 18.5 mm. The port of FIG. 36C, with the same top but with a rounded base would require an incision of about 14 mm, while having an incision circle (dotted inner circle) of about 13 mm. The port of FIG. 36B, with the same top as both depicted in FIG. 36A and FIG. 36C but with a flat base the same size as the top, would require an intermediate length incision, about 16 mm to 17 mm in length, while having an incision circle (dot-dash middle circle) of about 15 mm. All dimensions are in millimeter (mm).

Discussion

Concepts within this document include: (1) the "core port," which is a geometric shape used to characterize the central portion of any portacatheter; (2) "extensions," which are structural additions around the core port, and (3) the "incision circle," which models the skin incision length necessary to deliver a port into the subcutaneous tissues.

With respect to the core port, this document distinguishes a "functional core port" from a "geometric core port."

The functional core port may be represented as an upright cylinder, with a circular top corresponding to the port drum and surrounding rim, with a flat base of the same size as the top, and with a cylindrical side extending from the top to the base. This is the portion of a port comprising a reservoir into which a Huber needle is inserted.

The geometric core port, on the other hand, is used in this document to characterize the underlying shape of a port. While the geometric core top is the same as the functional core top, the geometric core base may be wider than, the same size as, or narrower than the top. However, embodiments of the invention do include ports wherein the geometric core port and the functional core port are the same shape, for example in FIGS. 7B, 13B, 34C, 35A and 35B. In this document, unless otherwise specified, a "core port" refers to the geometric core port.

A port can be characterized as a core port with added structural extensions. As provided herein, a method to define the underlying core port of a known portacatheter is described, as well as a method to identify known structural extensions.

With respect to the Structural Invention, known ports are distinguished from port embodiments of the invention in the following fashion: known ports are characterized in this document as core ports plus extensions; in contrast, selected inventive ports are characterized as core ports but with embodiments that comprise novel extensions.

The core port of known ports varies, but all presently known core ports comprise bases that are larger than the top. On the other hand, in embodiments, inventive port bases may be any size in relation to the size of the top, including larger than the top, smaller than the top, or even absent, e.g., as is shown in FIGS. 6 and 7. This is because embodiments of the ports comprise stabilizing extensions of the invention, which permits an embodiment of the port to be stable in the pocket while comprising a narrow flat base or even no flat base.

Figure 7H:
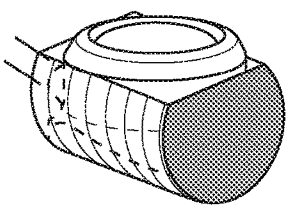

If a port embodiment has an underlying core port comprising a base that is smaller than the top, then the port has a narrow base and would therefore fit through a smaller incision. If an embodiment of the port has an underlying core port with a base that is a point, for example as shown in FIG. 7D, rather than a circle, for example as shown in FIG. 7C, then the port has a rounded base with no flat portion, as shown in FIG. 7H. Such a port would fit through a very small incision, smaller than those depicted in FIGS. 7E, F and G.

An example of a very small incision associated with a rounded base is illustrated in FIG. 36. FIG. 36A depicts a low-profile port with lateral extensions but with a broad base. FIG. 36B depicts the same port, except the base has been narrowed to match the top. FIG. 36C depicts a port with the same top as the other 2 ports, but with a rounded base. The port of FIG. 36C would fit through a 14 mm incision, whereas the port with a broad base would require an incision of just under 20 mm.

The geometric core port, or core port, concept is illustrated in FIGS. 6 and 7. All known ports comprise a core port with the base wider than the top, as shown in FIGS. 6A and 7A. Port embodiments may comprise a core port with a base that is wider than, the same size as, or narrower than the top, as exemplified in FIGS. 6A, 6B and 6C. In FIG. 6B, the geometric core port and the functional core port coincide (i.e., a cylinder), since the base and top are circles of the same size. Ports may also comprise a rounded base with no flat segment, as shown in FIGS. 6D and 7D. Another example of a core port with no flat segment is the Seldinger port of FIG. 3.

The incision circle is used as a concept to demonstrate the relationship between port design and the incision necessary to insert the port through the skin. The actual aperture created by inserting a port through an incision is not a perfect circle. When a known port, with a roughly trapezoidal cross-section, is advanced through an incision, the aperture partially conforms to the trapezoidal contour, forming a shape such as that demonstrated in FIGS. 12,13, 14, and 15. As shown, the top and bottom of the aperture are partially flattened, whereas the sides of the aperture, corresponding to the limits of the incision, do not conform to the sides of the trapezoid. The points of greatest resistance to passing the port through the skin are at the angles of the trapezoid and, to a lesser extent, at the top and the base.

Because the aperture does not conform to the sides of the port, there is laxity along the sides of the port during insertion. Ports, with sides that extend beyond the base, exploit this lateral laxity to include side structures that stabilize the port in the pocket. In effect, the port structure takes advantage of the lateral laxity by adding stabilizing structures at the port mid-plane that fit within the same incision as would be required if there were no added structures.

Because the incision circle only provides an approximation of the incision necessary to deliver a port, it is used primarily herein to rank order the size of an incision necessary for port insertion. That is, if, e.g., "Port A" fits through a smaller incision circle than Port B, then in real life Port A would generally also fit through a real incision that is smaller than the minimal incision used for implantation of Port B.

FIGS. 12, 14, and 15 illustrate the relationship between an actual incision and the incision circle. The shape of an actual incision is shown in FIG. 12A, which is a photograph taken during a port incision. In subsequent figures, the incision shape is approximated from the photograph. In FIGS. 12B and 12C, an incision circle is superimposed on the approximated actual incision shape. Both the incision circle and the approximated actual incision of FIG. 12B (the known port) are larger than the incision circle and approximated actual incision of FIG. 12C (an embodiment of the invention).

The use of a guidewire to facilitate catheter insertion or exchanges is generally referred to as the Seldinger technique, and selected embodiments of the invention are termed a Seldinger port, as exemplified in FIG. 3. Other examples and disclosures can be combined with or be modified to be a Seldinger port by comprising a lumen for the guidewire and a sealing mechanism for the back aperture.

The Seldinger technique has broad application in medicine. Generally, in the field of interventional radiology and other fields that utilize the Seldinger technique, catheters with a circular cross-section are advanced through small incisions. When the device cross-section is circular, roughly circular, or elliptical, the diameter of the device cross-section determines the incision length necessary to pass a device through the skin, which is generally the diameter of the device plus 1-2 mm. Because of the elasticity of the soft tissues, the catheter passes through the incision in a fashion that gently stretches the subcutaneous soft tissues around the catheter profile.

An advantage of using a Seldinger technique is that implantation is typically fast and easy, and the spaces created by dilators or balloons are of a reproducible size. The uniformity of dilatation means that there would be a predictably favorable fit if such a technique were used at the time of port insertion. A Seldinger approach to portacatheter design is also described in Applicant's U.S. Ser. Nos. 63/461,044, 18/439,985 and 63/644,885. As demonstrated in Applicant's U.S. Ser. Nos. 63/461,044 and 18/439,985, an over-the-wire portacatheter could be used in exchanges in the setting of hemodialysis access preservation. Applicant's U.S. Ser. Nos. 63/461,044, 18/439,985 and 63/644,885 are incorporated by reference in their entirety regarding methods of implantation of a catheter- or portacatheter-like device and the disclosed portacatheter devices.

In addition to the increased stability of port embodiments, the more rounded contour also facilitates the use of the Seldinger technique to fashion a subcutaneous pocket for port implantation. This is because the rounded cross-section of a port would create more uniform resistance as it passes through the port incision, and therefore the port would be easier to slide through the skin incision over a guidewire. That is, the rounded cross-section is less likely to snag at the skin than a known trapezoidal cross-section as the port is inserted.

Using the design elements described herein permits the designer options. A port may be designed to be inserted via the same incision as a known while comprising a larger drum. Alternatively, a port may be designed to be implanted via a smaller incision than a known port while comprising a drum of the same size. In embodiments, the designer could design a port with an 8 mm drum that can utilize a very small incision, as small as 14 mm.

Two ports may have the same overall width but be capable of passing through different incision lengths during insertion. For example, if known port A has an overall width W at the base, while embodiment port B has the same overall width W but at the equator, then port B will pass through a smaller incision than the minimally sized incision required by port A.

An example of the benefit of making the maximum width at the equator rather than the base is shown in FIG. 34. The stability benefit of the lateral extension component of the Structural Invention concept is demonstrated in comparing FIGS. 34A with 34B. The port in FIG. 34B is actually wider than the port of FIG. 34A, since they share the same base width but the port of FIG. 34B comprises lateral extensions (see FIG. 15 as an illustration). Nevertheless, FIG. 34B would fit through the same incision as FIG. 34A, and FIG. 34B would be more stable in the pocket based on added side friction and other factors described herein.

Some practitioners prefer to suture a port in place. If so, the wings or other extensions could act as a more convenient site to place a suture, which would save time and reduce the difficulty of implantation. For ease of potential suturing, the wings or extensions could have pre-positioned holes. The number of holes may be one, two, three, four, five, six, seven or eight, but preferably between two to four holes for sutures and adherence after implantation.

In the B. Braun Celsite Discreet port system, the port is generally inserted sideways through an up-and-down incision. In this design, the port is narrower from front to back than from left to right. Rotation around the long axis is resisted by a broad transverse width, and rotation around the short axis is resisted in part by the catheter acting as an anchor. This design permits a narrower base over the port short axis, which in turn permits a smaller incision. Nevertheless, the design still incorporates a flat base that is broader in both dimensions than the top or sides, and incorporation of design elements included herein would permit the base to be further narrowed, and the incision to be made shorter.

Although the disclosures herein refer specifically to single-lumen portacatheters, the concepts underlying the embodiments could be applied to double-lumen portacatheters in a straightforward fashion. The method is for purposes of illustration, and there are other methods by which a port of the invention could be implanted.

In an embodiment by which a Seldinger Portacatheter could be inserted, the following method also illustrates the use of dilators during portacatheter implantation.

1. After a small (<1 cm) incision, gain access in the standard fashion to the right internal jugular vein, leaving in place a peel-away sheath that extends to the superior vena cava.
2. Make a chest incision below the intended position of the port.
3. Tunnel from the chest wound to the venotomy wound, delivering a marked guidewire. Advance the guidewire via the peel-away sheath to the intended position for the tip of the portacatheter, then peel the sheath. Reduce the wire to form a smooth arc.
4. Run the dilator system over the guidewire, including a possible dissector dilator and complex dilators of progressively larger S2 segments.
5. Cut the catheter to size based on markers on the guidewire. Insert the Seldinger portacatheter over the guidewire.
6. Plug the portacatheter back end. Flush the port.
7. Close the wounds.

Embodiments

Structural Invention Embodiments

1. A portacatheter for implantation in a patient through a port incision, comprising:

a catheter in communication with the portacatheter, a base having a width, a length, a back end, and a front end, a geometric core port and one or more structural extensions, wherein the geometric core port has a shape comprising a left side, a right side, a front, a back, a circular base having a diameter, a circular top having a diameter, a height between the circular base and the circular top, and the left side and the right side extend between the circular base and the circular top, wherein the structural extension is selected from the group consisting of one or more of a base extension, a wing extension, and a lateral extension that is in contiguity with the core port, wherein the incision is defined by an incision circle, and wherein the combined geometric core port and one or more structural extensions fit through the same size incision circle as does the geometric core port without the one or more structural extensions.

2. The portacatheter of embodiment 1, wherein the lateral extension projects from the right side and the left side of the geometric core port, and the shape of the geometric core port combined with the lateral extension define a side width, a base width, and top width, wherein the side width is greater than both the base width and the top width by at least about 2 mm.

3. The portacatheter of embodiment 1, wherein the portacatheter is defined by a base plane rectangle having corners, wherein the base extension projects from the circular base, and comprises a shape, a height, and a configuration, wherein the shape and the configuration of the base extension comprises surfaces that project to and completely include surfaces at the corners of the base plane rectangle.

4. The portacatheter of embodiment 1, wherein the wing extension projects from the front, back, or top, or in any combination thereof, of the geometric core port and wherein the wing extension comprises a shape, a height, and a configuration.

5. The portacatheter of embodiment 1, wherein the diameter of the core port circular base is larger, about the same size, smaller, or is a single point as compared to the diameter of the circular top.

6. The portacatheter of embodiment 2, wherein the shape of the geometric core port combined with the lateral extension comprises a side width that is greater than both the width of the base and the width of the top by about 2 mm to about 10 mm.

7. The portacatheter of embodiment 2, wherein the incision circle has a transverse diameter along a minor axis, wherein the portacatheter has a maximum width at about the transverse diameter of the incision circle that is about equal to or greater than the diameter of the incision circle by about 1 mm to about 10 mm.

8. The portacatheter of embodiment 2, wherein the portacatheter is further defined as having a port long-axis silhouette comprising a top, a base, and sides, wherein the top is flat, the base and sides are rounded or roughly circular.

9. The portacatheter of embodiment 8, wherein the port long-axis silhouette comprises a top that is flat having a width, and a base that is flat having a width, wherein the width of the base is about the same size as or less than the width of the top.

10. The portacatheter of embodiment 2, wherein the lateral extensions are further defined by lateral sidewall rectangles that define the position at which lateral sidewalls project from the geometric core port, wherein the lateral sidewalls have a planar shape, multiple planar shapes, rounded shapes, or any combination of shapes thereof, each having a length.

11. The portacatheter of embodiment 10, wherein the lateral sidewalls are wider than the diameter of the base and the diameter of the top over the length of the portacatheter or over a subset of the length of the portacatheter, wherein the length of the lateral sidewalls are longer than the diameter of the geometric core port, and wherein the lateral sidewalls extend in front of, behind, or both in front of and behind the geometric core port.

12. The portacatheter of embodiment 3, wherein the portacatheter is further defined by a base plane square encompassing the geometric core port, wherein the port base rectangle extends beyond the port base square both in front of and behind the base plane square by about 2 mm to about 10 mm, wherein the portacatheter base comprises a rectangular shape, multiple rectangle shapes, curved shapes, or any combination of shapes thereof, comprising flat surfaces at the corners of the base plane rectangle.

13. The portacatheter of embodiment 3, wherein the base extension is planar and the height is about 1 mm, about 2 mm, about 3 mm, about 4 mm, or about 5 mm.

14. The portacatheter of embodiment 13, wherein the base extension has a height greater than 3 mm, and is contiguous with either:

a) the lateral extension that is defined by a side width that is greater than both a base width and a top width by at least about 2 mm, or b) the wing extension that projects from the front, back, or top, or in any combination thereof, or c) a combination of a) and b).

15. The portacatheter of embodiment 1, comprising a retention cuff located either at the back end of the port, the front end of the port, or the front end and back end of the portacatheter.

16. The portacatheter of embodiment 1, wherein the wing extension is a fixed structure and extends either in front of, behind, or both in front of and behind the geometric core port by about 3 mm to about 10 mm.

17. The portacatheter of embodiment 1, wherein the wing extension is expanding and made of plastic or a metal comprising nitinol.

18. The portacatheter of embodiment 1, wherein the catheter extends into a space other than the intravenous space.

19. The portacatheter of embodiment 1, further comprising one or more port drums and lumens, wherein the port drum is aligned along a major axis of the geometric core port.

The embodiments disclosed below are additional embodiments.

20. A port of a portacatheter, wherein the side width is greater than the base and top width by at least 2 mm.

21. A port of a portacatheter, wherein the port base extends in front of and behind the port in a fashion that includes surfaces at the corners of a base plane rectangle, and a. the base plane rectangle width is approximately the same as the core port base diameter; and b. the base plane rectangle extends at least 2 mm beyond the front and beyond the back of the base plane square.

22. A port of a portacatheter comprising wings at a level above the base extending in front of, behind, or both in front of and behind the port, such that the wings fit within the incision circle of the core port.

23. The port of embodiment 1, wherein the base is wider than the top.

24. The port of embodiment 1, wherein the top is wider than the base.

25. The port of embodiment 1, wherein the side width exceeds the base and top width by 2-5 mm.

26. The port of embodiment 1, wherein the side width exceeds the base and top width by 5-10 mm.

27. The port of embodiment 1, wherein the base is rounded in cross-section, with a flat base width of zero.

28. The port of embodiment 1, wherein the port fits within the incision circle of the core port.

29. The port of embodiment 1, wherein the port silhouette, except for the top, is roughly circular.

30. The port of embodiment 1, wherein portions of the port cross-sections are roughly circular.

31. The port of embodiment 1, wherein the lateral-most portion of the silhouette comprises at least 1 flat surface.

32. The port of embodiment 1, wherein the lateral sidewalls project outward from the lateral sidewall rectangles in a planar shape or in multiple planar shapes.

33. The port of embodiment 1, wherein the lateral sidewalls extend outward in a shape or shapes that combine planar shapes and rounded surfaces.

34. The port of the embodiment 1, wherein the lateral sidewalls are wider than the base and the top over the length of the core port.

35. The port of the embodiment 1, wherein the lateral sidewalls are longer than the core port, extending in front of, behind, or both in front of and behind the core port.

36. The port of embodiment 1, wherein the lateral sidewalls are wider than the base and the top over a subset of the length of the port.

37. The port of embodiment 1, wherein the maximum width of the port occurs at or near the transverse diameter of the incision circle, with a width roughly equal to the incision circle diameter.

38. The port of embodiment 1, wherein the maximum width of the port occurs at or near the transverse diameter of the incision circle, with a width greater than the incision circle diameter.

39. The port of embodiment 1, wherein the maximum width of the port occurs at or near the transverse diameter of the incision circle, with a width greater than the incision circle diameter by 1 to 5 mm.

40. The port of embodiment 1, wherein the maximum width of the port occurs at or near the transverse diameter of the incision circle, with a width greater than the incision circle diameter by 5 to 10 mm.

41. The port of embodiment 2, wherein the port base rectangle is 2-10 mm longer than the core port diameter.

42. The port of embodiment 2, wherein the port base rectangle is 10-20 mm longer than the core port diameter.

43. The port of embodiment 2, wherein the base port rectangle extends in front of the core port by 1-10 mm.

44. The port of embodiment 2, wherein the base port rectangle extends behind the core port by 1-10 mm.

45. The port of embodiment 2, wherein the base extensions are roughly planar, with a height less than or equal to 3 mm.

46. The port of embodiment 2, wherein the base extensions have a height greater than 3 mm.

47. The port of embodiment 2, wherein the upper margins of the base extensions continue in the height dimension up to a port side of embodiment 1.

48. The port of embodiment 2, wherein the upper margins of the base extensions continue in the height dimension up to a wing or wings of embodiment 3.

49. The port of embodiment 3, wherein the wings extend in front of the core port by 3-10 mm.

50. The port of embodiment 3, wherein the wings extend behind the core port by 3-10 mm.

51. The port of embodiment 3, wherein the wings extend both in front of and behind the port by 3-10 mm.

52. The port of embodiments 1, 2 and 3, wherein there are expanding wings incorporated into the port.

53. The port of embodiments 1, 2 and 3, wherein the expanding wings are made of nitinol.

54. The port of embodiments 1, 2 and 3, wherein the expanding wings are made of plastic.

55. The port of embodiments 1, 2 and 3, wherein the expanding wings are made of a metal other than nitinol.

56. The port of embodiments 1, 2 and 3, wherein a retention cuff is included over a portion of the surface of the port.

57. The port of embodiments 1, 2 and 3, wherein a retention cuff is roughly circumferential and located at the back end of the port.

58. The port of embodiments 1, 2 and 3, wherein a retention cuff is roughly circumferential and located at the front end of the port.

59. The port of embodiments 1, 2 and 3, wherein a retention cuff is roughly circumferential and located over a less than 20% length of the port.

60. The port of embodiments 1, 2 and 3, wherein a retention cuff is roughly circumferential and located over a greater than 20% length of the port.

61. The port of embodiments 1, 2 and 3, wherein there is more than 1 retention cuff.

62. The port of embodiments 1, 2 and 3, wherein the catheter extends from the port into a space other than an intravenous position.

63. The ports of embodiment 1, 2 and 3, wherein there are 2 port drums and lumens, with the drums aligned along the major axis of the port.

Dilator Invention Embodiments

64. Devices comprising a guidewire or guidewires, a tunneler, a dilator, a combination of dilators, a balloon, or a combination of a dilator and a balloon that may be used to fashion a pocket for a portacatheter.

65. Devices comprising a trocar that may be used to fashion a pocket for a portacatheter.

66. The device of embodiment 45 comprising a single dilator.

67. The device of embodiment 45 comprising multiple dilators.

68. The device of embodiment 45 comprising a balloon.

69. The device of embodiment 45 comprising a combination of a dilator and a balloon.

70. A device of embodiment 45, wherein the dilator comprises:

- a. a front end, distal segment (S1) with a length L1 and a roughly circular cross-section of maximal diameter D1,
- b. a transition segment,
- c. a backend, proximal segment (S2) with a length L2 and either a roughly,
- d. circular or a non-circular polygonal cross section with maximal diameter D2, and
- e. wherein D2 is greater than D1.

71. The device of embodiment 51, wherein D1 is about the same size as or 10-30% larger than the diameter of the catheter of a portacatheter for implantation.

72. The device of embodiment 51, wherein D2 is about the diameter of the maximal diameter of the port for implantation.

73. The device of embodiment 51, wherein S2 has a roughly circular cross-section.

74. The device of embodiment 51, wherein S2 has a polygonal cross-section.

75. The device of embodiment 55, wherein the S2 cross-section has sides of equal length.

76. The device of embodiment 55, wherein the S2 cross-section has sides of unequal length.

77. The device of embodiment 55, wherein the S2 cross-section is a trapezoid.

78. The device of embodiment 55, wherein the S2 cross-section is a rectangle or square.

79. The dilator of embodiment 51, wherein the transition segment is roughly conical, with a cross-section of maximal diameter D1 adjacent to S1 flaring to D2 adjacent to S2.

80. The dilator of embodiment 51, wherein the transition segment contains at least one sharpish leading edge that extends beyond the roughly conical contour of TS in a coronal plane.

81. The dilator of embodiment 51, wherein the transition segment contains at least one sharpish leading edge that extends beyond the roughly conical contour of TS in a coronal plane, with the leading edge at a level below the height level of the lumen.

82. The dilator of embodiment 51, wherein the transition segment contains at least one sharpish leading edge that extends beyond the roughly conical contour of TS in a coronal plane, with the leading edge at a level at or above the height level of the lumen.

83. The dilator of embodiment 51, wherein the transition segment contains more than 1 and less than 6 sharpish leading edges that extend beyond the roughly conical contour of the transition segment, roughly in a coronal plane.

84. The dilator of embodiment 51, wherein S1 has a roughly circular cross-section.

85. The dilator of embodiment 51, wherein L1 is between 0 and 30 cm.

86. The dilator of embodiment 51, wherein L2 is between 2 and 10 cm.

87. The dilator of embodiment 51, wherein L2 is the length of the port segment of the portacatheter.

88. The dilator of embodiment 51, wherein L2 is the length of the port segment of the portacatheter plus 1-4 cm or 10-80% longer than the portacatheter.

89. The devices of embodiment 51, comprising:

a. a first dilator, which may be simple or complex, and b. a second dilator, which may be simple or complex.

90. The dilators of embodiment 48, wherein the first dilator is simple.

91. The dilators of embodiment 48, wherein the first dilator is simple and has a cross-sectional diameter of between 5F and 10F.

92. The dilators of embodiment 48, wherein the first dilator is complex.

93. A device of embodiment 48, wherein a first dilator comprises:

a. a front end, distal segment (S1F) with a length L1F and a roughly circular cross section of maximal diameter D1F, b. a transition segment (TSF), and c. a back end, proximal segment (S2F) with a length L2F and either a roughly circular or a non-circular polygonal cross section with maximal diameter D2F;

wherein D2F is greater than D1F.

94. A device of embodiment 48, wherein a second dilator comprises:

a. a front end, distal segment (S1S) with a length L1S and a roughly circular cross section of maximal diameter D1S, b. a transition segment, and a back end, proximal segment (S2S) with a length L2S and either a roughly circular or a non-circular polygonal cross section with maximal diameter D2S, and c. wherein D2S is greater than D1S.

95. The device of embodiment 74, wherein D1F is about the diameter or slightly larger than the diameter of the catheter of a portacatheter for implantation.

96. The device of embodiment 74, wherein D2F is between 20% and 80% of the diameter of the maximal diameter of the port for implantation.

97. The device of embodiment 74, wherein S2F has a roughly circular cross-section.

98. The device of embodiment 74, wherein S2F has a polygonal cross-section.

99. The device of embodiment 75, wherein the S2F cross-section has sides of equal length.

100. The device of embodiment 75, wherein the S2F cross-section has sides of unequal length.

101. The device of embodiment 75, wherein the S2F cross-section is a trapezoid.

102. The device of embodiment 75, wherein the S2F cross-section is a rectangle or square.

103. The dilator of embodiment 75, wherein the transition segment is roughly conical, with a cross-section of maximal diameter D1F adjacent to S1F flaring to D2F adjacent to S2F.

104. The dilator of embodiment 75, wherein the transition segment contains at least one sharpish leading edge that extends beyond the roughly conical contour of transition segment F (TSF).

105. The dilator of embodiment 75, wherein the transition segment contains more than 1 sharpish leading edge that extends beyond the roughly conical contour of TSF.

106. The dilator of embodiment 75, wherein S1F has a roughly circular cross-section.

107. The dilator of embodiment 72, wherein L1F is between 0 and 30 cm.

108. The dilator of embodiment 75, wherein L2F is between 2 and 10 cm.

109. The dilator of embodiment 75, wherein L2F is approximately the length of the port segment of the portacatheter.

110. The dilator of embodiment 75, wherein L2F is the length of the port segment of the portacatheter plus 1-4 cm or 10-80% longer than the portacatheter.

111. The device of embodiment 75, wherein D1S is about the diameter or 10-30% larger than the diameter of the catheter of a portacatheter for implantation.

112. The device of embodiment 75, wherein D2S is about the diameter of the maximal diameter of the port for implantation.

113. The device of embodiment 75, wherein S2S has a roughly circular cross-section.

114. The device of embodiment 75, wherein S2S has a polygonal cross-section.

115. The device of embodiment 75, wherein the S2S cross-section has sides of equal length.

116. The device of embodiment 75, wherein the S2S cross-section has sides of unequal length.

117. The device of embodiment 75, wherein the S2S cross-section is a trapezoid.

118. The device of embodiment 75, wherein the S2S cross-section is a rectangle or square.

119. The dilator of embodiment 75, wherein the transition segment is roughly conical, with a cross-section of maximal diameter D2S adjacent to S1S flaring to D2S adjacent to S2S.

120. The dilator of embodiment 75, wherein the transition segment contains at least one sharpish leading edge that extends beyond the roughly conical contour of TSS.

121. The dilator of embodiment 75, wherein the transition segment contains more than 1 sharpish leading edge that extends beyond the roughly conical contour of TSS.

122. The dilator of embodiment 75, wherein S1S has a roughly circular cross-section.

123. The dilator of embodiment 75, wherein L1S is between 0 and 30 cm.

124. The dilator of embodiment 75, wherein L2S is between 2 and 10 cm.

125. The dilator of embodiment 75, wherein L2S is approximately the length of the port segment of the portacatheter.

126. The dilator of embodiment 75, wherein L2S is the length of the port segment of the portacatheter plus 1-4 cm or 10-20% longer than the portacatheter.

127. The devices of embodiments 74 and 75, wherein the height of the dilator is less than the width over the S2 and transitional segments.

128. The tunneler of embodiment 45, wherein there is a central lumen.

129. The tunneler of embodiment 45, wherein the central lumen measures 0.018, 0.035, or 0.038 inch.

130. The tunneler of embodiment 45, wherein the central lumen is larger than 0.038 inch, such as 0.045 inch or larger.

131. A guidewire of embodiment 45, wherein the wire ranges in diameter from 0.014 to 0.45 inch.

132. A guidewire of embodiment 45, wherein the wire is 0.035 or 0.38 inch.

133. The dilators of embodiment 75, wherein any or all the dilators of a dilator series comprise the features listed for the single dilator of embodiment 45.

134. The device of embodiment 51, wherein a component dilator has a higher width:height ratio (is flatter) and may have a sharpish leading edge over the lateral aspect of the S2 segment.

135. The dilators of embodiment 51, wherein a handle is attached to the hub.

136. The dilators of embodiment 45, wherein one of the dilators comprises a balloon in the proximal portion.

137. A dilator of embodiment 45, wherein the height of the dilator is less than 50% of the width of the dilator.

138. A dilator of embodiment 45, wherein the height of the dilator is less than 50% of the width of the dilator, and the dilator comprises sharpish flat lateral leading edges.

139. A trocar of embodiment 46, wherein the proximal portion comprises sharpish flat lateral leading edges.

140. A trocar of embodiment 46, wherein the proximal portion comprises a balloon.

141. A method of arm portacatheter implantation comprising the following steps (used for illustration and not limiting):

a. identify a large vein, either axillary, basilic, brachiocephalic, in the upper arm and mark the location; after anesthesia, make a skin nick at the site and loosen it with a Kelly clamp; via the skin nick, select the vein using a small needle in a central direction. Using Seldinger technique, establish a peel-away sheath.

b. deliver a catheter via the peel-away sheath to the desired central location near the SA junction, then pull back approximately 3 cm;

c. identify a preferred site for the port, typically over the more distal medial arm above the elbow. After anesthesia, make a 14-15 mm incision or skin nick, then loosen the incision with a Kelly clamp;

d. tunnel from the port incision/nick to the venotomy nick, establishing a guidewire from the port site to the venotomy;

e. over the guidewire, use dilators and/or an angioplasty balloon to fashion a pocket for the port;

f. deliver the catheter from the venotomy to the port site:

i. over the guidewire, deliver a device designed to attach to the catheter and make the attachment; pull the catheter back from the venotomy to the port site (the tunneler may be used for this step); or ii. slide the venous catheter over the guidewire until it appears at the port site; remove the guidewire and pull the catheter back until the loop at the venotomy site is no longer present;

g. attach the port to the venous catheter; deliver the mated port/connector into the port pocket;

h. flush the port;

i. close the wounds using Steri-Strips, Dermabond, sutures or some combination.

142. The method of embodiment 122, further comprising establishing the wire from the port incision to the venotomy incision.

Seldinger Invention Embodiments

143. A portacatheter comprising a closeable aperture in the back of the port aligned with the major axis of the catheter.

144. The portacatheter of embodiment 124, wherein the aperture comprises a valve.

145. The portacatheter of embodiment 124, wherein the aperture may be closed using a device other than a valve.

146. The portacatheter of embodiment 124, wherein the device used to close the back aperture uses a screw to seal the aperture.

147. The portacatheter of embodiment 124, wherein the device to close the back aperture snaps into the aperture.

148. The portacatheter of embodiment 124, wherein the device used to close the aperture includes an external portion that comprises an anchoring device.

149. The portacatheter of embodiment 129, wherein the anchoring device is a wing of the invention.

150. The portacatheter of embodiment 129, wherein the anchoring device includes a retention cuff.

151. The portacatheter of embodiment 124, wherein the aperture at the back end measures between 0.018 and 0.045 inch.

152. The portacatheter of embodiment 124, wherein the aperture at the back end measures between 0.018 inch and 5 mm.

153. The portacatheter of embodiment 124, wherein there is a taper from the reservoir to the aperture to guide a wire into the aperture.

What is claimed:

1. A portacatheter for implantation in a patient through a port incision, comprising:

a catheter in communication with the portacatheter, a base having a width, a length, a back end, and a front end, a geometric core port and one or more structural extensions, wherein the geometric core port has a shape comprising a left side, a right side, a front, a back, a circular base having a diameter, a circular top having a diameter, a height between the circular base and the circular top, and the left side and the right side extend between the circular base and the circular top, wherein the one or more structural extensions are selected from the group consisting of one or more base extensions, one or more wing extensions, and one or more lateral extensions that are in contiguity with the geometric core port, wherein the geometric core port defines an incision circle, wherein the one or more lateral extensions project from the right side and the left side of the geometric core port, and the shape of the geometric core port combined with the one or more lateral extensions define a side width, a base width, and a top width of the portacatheter, wherein the side width of the portacatheter is greater than both the base width and the top width of the portacatheter by at least about 2 mm, wherein the combined geometric core port and one or more structural extensions fit through the same size incision as does the geometric core port without the one or more structural extensions; and wherein the portacatheter base is defined by a base plane and a base plane rectangle, wherein the base plane rectangle is defined as a rectangular subset of the base plane having corners, wherein the base plane rectangle comprises the one or more base extensions and the circular base of the geometric core port, wherein the one or more base extensions project from the circular base of the geometric core port within the base plane, and comprise a shape, a height, and a configuration, wherein the shape and the configuration of the one or more base extensions comprises surfaces that project from the circular base of the geometric core port and completely include surfaces at the corners of the base plane rectangle.

2. The portacatheter of claim 1, wherein the portacatheter base is further defined by a core base plane square encompassing the circular base of the geometric core port, wherein the base plane rectangle extends beyond the core base plane square both in front of and behind the core base plane square by about 2 mm to about 10 mm, wherein the portacatheter base further comprises a rectangular shape, multiple rectangle shapes, curved shapes, or any combination of said shapes thereof in front of or behind the base plane rectangle, while comprising flat surfaces at the corners of the base plane rectangle.

3. The portacatheter of claim 1, wherein at least one or more of the base extensions are planar, and the height is about 1 mm, about 2 mm, about 3 mm, about 4 mm, or about 5 mm.

4. The portacatheter of claim 3, wherein the one or more base extensions has a height greater than 3 mm, and is contiguous with either:

a) the one or more lateral extensions that are defined by a side width that is greater than both a base width and a top width by at least about 2 mm, or b) the one or more wing extensions that project from the front, back, or top, or in any combination thereof, or c) a combination of a) and b).

5. The portacatheter of claim 1, wherein the one or more wing extensions project from the front, back, or top, or in any combination thereof, of the geometric core port and wherein the one or more wing extensions comprise a shape, a height, and a configuration.

6. The portacatheter of claim 1, wherein the diameter of the geometric core port circular base is larger, about the same size, smaller, or is a single point as compared to the diameter of the circular top of the geometric core port.

7. The portacatheter of claim 1, wherein the shape of the geometric core port combined with the one or more lateral extensions comprise a side width that is greater than both the width of the base and the diameter of the top by about 2 mm to about 10 mm.

8. The portacatheter of claim 1, wherein the incision circle has a transverse diameter along a minor axis, wherein the portacatheter has a maximum width at about the transverse diameter of the incision circle that is about equal to or greater than the diameter of the incision circle by about 1 mm to about 10 mm.

9. The portacatheter of claim 1, wherein the portacatheter is further defined as having a port long-axis silhouette comprising a top, a base, and sides, wherein the top is flat, the base and sides are rounded or roughly circular.

10. The portacatheter of claim 9, wherein the sides of the port long-axis silhouette are fully bilaterally symmetrical about a mid-sagittal plane of the portacatheter.

11. The portacatheter of claim 10, wherein the portacatheter has an equatorial level, wherein the equatorial level corresponds to a plane parallel with the base of the port located near midway between the circular top and the circular base, and wherein the portacatheter has a maximum width at the equatorial level that is about equal to the diameter of the incision circle.

12. The portacatheter of claim 10, wherein the portacatheter has an equatorial level, wherein the equatorial level corresponds to a plane parallel with the base of the port located near midway between the circular top and the circular base, and wherein the portacatheter has a maximum width at the equatorial level that is greater than the diameter of the incision circle by about 1 mm to about 10 mm.

13. The portacatheter of claim 10, wherein the portacatheter has an equatorial level, wherein the equatorial level corresponds to a plane parallel with the base of the port located near midway between the circular top and the circular base, and wherein the portacatheter has a maximum width at the equatorial level that is greater than the diameter of the incision circle by 2 mm to 3 mm.

14. The portacatheter of claim 1, wherein the portacatheter is further defined as having a port long-axis silhouette comprising a top that is flat having a width, and a base that is flat having a width, wherein the width of the base is about the same size as or less than the width of the top.

15. The portacatheter of claim 1, wherein the one or more lateral extensions are further defined by lateral sidewall rectangles that define the position at which lateral sidewalls project from the geometric core port, wherein the lateral sidewalls have a planar shape, multiple planar shapes, rounded shapes, or any combination of said shapes thereof, each having a length.

16. The portacatheter of claim 15, wherein the lateral sidewalls are wider than the diameter of the geometric core port base and the diameter of the geometric core port top over the length of the portacatheter or over a subset of the length of the portacatheter, wherein the length of the lateral sidewalls are longer than either the diameter of the geometric core port base or the diameter of the geometric core port top, and wherein the lateral sidewalls extend in front of, behind, or both in front of and behind the geometric core port.

17. The portacatheter of claim 1, having a back end of the portacatheter and a front end of the portacatheter, comprising a retention cuff located either at the back end of the portacatheter, the front end of the portacatheter, or the front end and the back end of the portacatheter.

18. The portacatheter of claim 1, wherein the one or more wing extensions are fixed structures and extend either in front of, behind, or both in front of and behind the geometric core port by about 3 mm to about 10 mm.

19. The portacatheter of claim 1, wherein the one or more wing extensions are expanding and made of plastic or a metal comprising nitinol.

20. The portacatheter of claim 1, wherein the catheter extends into a space of a subject, wherein the space of the subject is other than an intravenous space.

21. The portacatheter of claim 1, further comprising one or more port drums and lumens, wherein the port drum is aligned along a major axis of the geometric core port.

22. A portacatheter for implantation in a patient through a port incision, comprising:

a catheter in communication with the portacatheter;

a base having a width, a length, a back end, and a front end; wherein the length is longer than the width;

a geometric core port and one or more structural extensions, wherein the geometric core port has a shape comprising a left side, a right side, a front, a back, a circular base having a diameter, a circular top having a diameter, a height between the circular base and the circular top, and an equatorial level, wherein the left side and the right side extend between the circular base and the circular top;

wherein the equatorial level corresponds to a plane parallel with the base of the port located near midway between the circular top and the circular base;

wherein the one or more structural extensions comprise one or more lateral extensions in contiguity with the geometric core port, and optionally comprise one or more base extensions and/or one or more wing extensions;

wherein one or more lateral extensions project from the right side and the left side of the geometric core port, and the shape of the geometric core port combined with the one or more lateral extensions define a side width, a base width, and a top width, wherein the side width is greater than both the base width and the top width by at least about 2 mm;

wherein a widest portion of the combined geometric core port and the one or more structural extensions is at or near an equatorial level;

wherein the portacatheter has a long-axis silhouette in a generally ovoid shape comprising a left side, a right side, and a mid-sagittal plane, wherein over a range from the level of the circular base up to the equatorial level, a lateral distance from the mid-sagittal plane of the portacatheter to an exterior contour of the combined geometric core port and the one or more structural extensions, excluding any base extension, is increasing with increasing height from the level of the circular base; and wherein any base extension and any wing extension, when present, does not extend laterally beyond the long-axis silhouette of the geometric core port combined with the one or more lateral extensions.

23. The portacatheter for implantation in a patient through a port incision of claim 22, wherein, over the range from the level of the circular base up to the equatorial level, a lateral distance from the mid-sagittal plane of the portacatheter to an exterior contour of the combined geometric core port and the one or more structural extensions, excluding any base extensions, does not define any corner having an included angle less than 90 degrees.

24. The portacatheter for implantation in a patient through a port incision of claim 22, wherein the one or more structural extensions comprise an equatorial planar surface projecting laterally from at least one of the left side and the right side at or near the equatorial level.

25. The portacatheter for implantation in a patient through a port incision of claim 22, wherein the port incision is defined by an incision circle having a diameter, and wherein a maximum transverse width at or near the equatorial level is equal to the diameter of the incision circle.

26. The portacatheter for implantation in a patient through a port incision of claim 22, wherein the port incision is defined by an incision circle having a diameter, and wherein a maximum transverse width at or near the equatorial level of the portacatheter is greater than the diameter of the incision circle by about 1 mm to about 10 mm.

* * * * *